US012653376B2

(12) United States Patent
Uyama et al.

(10) Patent No.: US 12,653,376 B2
(45) Date of Patent: Jun. 16, 2026

(54) BIOLOGICAL IMAGE PROCESSING APPARATUS, METHOD, NON-TRANSITORY COMPUTER READABLE MEDIUM AND BIOLOGICAL IMAGE PROCESSING SYSTEM

(71) Applicant: Sony Corporation, Tokyo (JP)

(72) Inventors: Keisuke Uyama, Kanagawa (JP); Tsuneo Hayashi, Tokyo (JP); Koji Kashima, Kanagawa (JP); Masahito Yamane, Kanagawa (JP)

(73) Assignee: Sony Corporation, Tokyo (JP)

( * ) Notice: Subject to any disclaimer, the term of this patent is extended or adjusted under 35 U.S.C. 154(b) by 1126 days.

(21) Appl. No.: 16/982,048

(22) PCT Filed: Mar. 12, 2019

(86) PCT No.: PCT/JP2019/009863
§ 371 (c)(1),
(2) Date: Sep. 18, 2020

(87) PCT Pub. No.: WO2019/181632
PCT Pub. Date: Sep. 26, 2019

(65) Prior Publication Data
US 2021/0015343 A1 Jan. 21, 2021

(30) Foreign Application Priority Data
Mar. 20, 2018 (JP) ................................ 2018-052776

(51) Int. Cl.
*A61B 1/00* (2006.01)
*A61B 1/045* (2006.01)

(52) U.S. Cl.
CPC ........ *A61B 1/0005* (2013.01); *A61B 1/00042* (2022.02); *A61B 1/00048* (2013.01); *A61B 1/045* (2013.01)

(58) Field of Classification Search
CPC .............. A61B 1/0005; A61B 1/00042; A61B 1/00048; A61B 1/045
See application file for complete search history.

(56) References Cited

U.S. PATENT DOCUMENTS 5,817,019 A * 10/1998 Kawashima .......... G01S 15/894
128/916
2005/0215854 A1 * 9/2005 Ozaki ................ A61B 1/00042
600/101

(Continued)

FOREIGN PATENT DOCUMENTS

CN 1874734 A 12/2006
CN 101006928 A 8/2007

(Continued)

OTHER PUBLICATIONS

International Search Report and Written Opinion mailed on Jun. 14, 2019 for PCT/JP2019/009863 filed on Mar. 12, 2019, 11 pages.

*Primary Examiner* — Michael J Carey
*Assistant Examiner* — William B Chou
(74) *Attorney, Agent, or Firm* — XSENSUS LLP

(57) ABSTRACT

A surgical assistance apparatus includes circuitry configured to generate a first image to be displayed in a first display region and including a first operative field image of a surgical subject and a first visual annotation image superimposed on a predetermined region in an operative field of the first operative field image that corresponds to a physical region of the surgical subject. The circuitry is also configured to generate a second image to be displayed in a second display region and including a second operative field image and a second visual annotation image superimposed on an estimated region of the second operative field image that corresponds to the physical region of the surgical subject.

19 Claims, 28 Drawing Sheets

BEFORE ANNOTATION    AFTER ANNOTATION    ANNOTATION TRACKS IMAGE

(56)                References Cited

U.S. PATENT DOCUMENTS

| | | | | |
|---|---|---|---|---|
| 2006/0079745 A1* | 4/2006 | Viswanathan | ......... | A61B 34/20 |
| | | | | 600/407 |
| 2007/0225553 A1* | 9/2007 | Shahidi | .................. | A61B 90/36 |
| | | | | 600/103 |
| 2010/0004539 A1 | 1/2010 | Chen | | |
| 2010/0317965 A1 | 12/2010 | Itkowitz et al. | | |
| 2011/0190774 A1* | 8/2011 | Nikolchev | ............. | A61B 34/10 |
| | | | | 606/86 R |
| 2013/0016198 A1* | 1/2013 | Higuchi | .................. | G06T 11/60 |
| | | | | 348/E7.085 |
| 2013/0023730 A1 | 1/2013 | Kitamura | | |
| 2013/0211232 A1* | 8/2013 | Murphy | .............. | A61B 1/0005 |
| | | | | 600/109 |
| 2014/0160264 A1* | 6/2014 | Taylor | .................... | A61F 9/008 |
| | | | | 348/79 |
| 2014/0303435 A1* | 10/2014 | Taniguchi | ............. | G06T 7/0016 |
| | | | | 600/103 |

| | | | | |
|---|---|---|---|---|
| 2015/0049163 A1* | 2/2015 | Smurro | ................. | H04L 65/403 |
| | | | | 348/14.08 |
| 2015/0051617 A1* | 2/2015 | Takemura | .............. | A61B 34/30 |
| | | | | 606/130 |
| 2015/0241685 A1 | 8/2015 | Saur et al. | | |
| 2015/0269229 A1 | 9/2015 | Shenoy | | |
| 2016/0210411 A1* | 7/2016 | Mentis | .................. | G06F 3/0304 |
| 2016/0212370 A1 | 7/2016 | Lee | | |
| 2017/0105701 A1 | 4/2017 | Pelissier | | |

FOREIGN PATENT DOCUMENTS

| | | |
|---|---|---|
| CN | 102274039 A | 12/2011 |
| CN | 102629376 A | 8/2012 |
| CN | 102821671 A | 12/2012 |
| JP | 08-107875 A | 4/1996 |
| JP | 2012-529970 A | 11/2012 |
| WO | 2013/179905 A1 | 12/2013 |

* cited by examiner

BEFORE ANNOTATION

AFTER ANNOTATION

ANNOTATION TRACKS IMAGE

BIOLOGICAL IMAGE PROCESSING APPARATUS, METHOD, NON-TRANSITORY COMPUTER READABLE MEDIUM AND BIOLOGICAL IMAGE PROCESSING SYSTEM

CROSS-REFERENCE TO RELATED APPLICATIONS

The present application is based on PCT filing PCT/JP2019/009863, filed Mar. 12, 2019, which claims priority to JP 2018-052776, filed Mar. 20, 2018, the entire contents of each are incorporated herein by reference.

TECHNICAL FIELD

The present disclosure relates to a surgery assistance system and a display method, and in particular, a surgery assistance system and a display method that are capable of improving communication between operators.

BACKGROUND ART

At some surgery sites, an advising doctor performs surgery assistance, such as the presentation of a region to be operated, in order to assist an inexperienced surgeon. Furthermore, in some cases, a plurality of surgeons advance surgery while consulting with each other. Accordingly, there is a need for medical equipment that has a function of clearly transmitting an instruction of one operator to another operator.

For example, PTL 1 discloses a three-dimensional observation apparatus that is capable of writing an annotation to a three-dimensional surgical image.

CITATION LIST

Patent Literature

PTL 1: WO 2013/179905 A

SUMMARY OF INVENTION

Technical Problem

However, in the conventional configuration, via a single operative field image, an advising doctor presents a region to be operated, or a surgeon confirms the presented region to be operated.

In this case, there is a probability that a motion to write an annotation to an operative field image by a first user disturbs an operator (i.e., a second user) who performs surgery while confirming the operative field image by obscuring the operative field image, and the operators (i.e., first and second users) fail to successfully perform communication with each other.

The present disclosure has been made in view of the situation described above, and according to an embodiment of the present disclosure, communication between operators can be improved.

Solution to Problem

A surgical assistance apparatus includes circuitry configured to generate a first image to be displayed in a first display region and including a first operative field image of a surgical subject and a first visual annotation image superimposed on a predetermined region in an operative field of the first operative field image that corresponds to a physical region of the surgical subject. The circuitry is also configured to generate a second image to be displayed in a second display region and including a second operative field image and a second visual annotation image superimposed on an estimated region of the second operative field image that corresponds to the physical region of the surgical subject.

A surgical method includes generating a first image to be displayed in a first display region and including a first operative field image of a surgical subject and a first visual annotation superimposed on a predetermined region of the first operative field image that corresponds to a physical region of the surgical subject, and generating a second image to be displayed in a second display region and including a second operative field image and a second visual annotation image superimposed on an estimated region of the second operative field image that corresponds to the physical region of the surgical subject.

A non-transitory computer readable medium storing instructions, which when executed by a computer cause the computer to perform steps including generating a first image to be displayed in a first display region and including a first operative field image of a surgical subject and a first visual annotation superimposed on a predetermined region of the first operative field image that corresponds to a physical region of the surgical subject; and generating a second image to be displayed in a second display region and including a second operative field image and a second visual annotation image superimposed on an estimated region of the second operative field image that corresponds to the physical region of the surgical subject.

A surgical assistance system includes an endoscope including an imager that captures a second operative field image of a surgical subject; circuitry configured to generate a first image to be displayed in a first display region and including a first operative field image of the surgical subject and a first visual annotation image superimposed on a predetermined region of the first operative field image that corresponds to a physical region of the surgical subject, and generate a second image to be displayed in a second display region and including the second operative field image and a second visual annotation image superimposed on an estimated region of the second operative field image that corresponds to the physical region of the surgical subject; and a surgical tool that is moved inside the surgical subject to perform a surgical procedure on the surgical subject under the control of a healthcare worker based on the second visual annotation image in the second image.

Advantageous Effects of Invention

According to an embodiment of the present disclosure, communication between operators can be improved.

BRIEF DESCRIPTION OF DRAWINGS

FIG. 4 is a block diagram illustrating detailed configuration examples of a sensing unit and an image data generator.

FIG. 16 is a diagram explaining a display mode of an operative field image.

FIG. 17 is a diagram explaining a display mode of an operative field image.

FIG. 18 is a diagram explaining a display mode of an operative field image.

FIG. 20 illustrates an example of the writing of an annotation to a past operative field image.

FIG. 21 illustrates an example of a masking display.

FIG. 22 illustrates an example of a preview display of a three-dimensional image.

FIG. 25 illustrates a display example of an annotation.

FIG. 26 illustrates a display example of an annotation.

FIG. 27 illustrates another configuration example of the surgery assistance system according to the embodiment.

FIG. 28 is a block diagram illustrating a hardware configuration example of an information processing device.

DESCRIPTION OF EMBODIMENTS

Embodiments of the present disclosure (hereinafter referred to as embodiments) are described below. Note that description will be made in the order described below.

1. System configuration
2. Flow of annotation writing processing
3. Display mode of operative field image
4. Variations
5. Application
6. Hardware configuration
7. Summary <1. System Configuration>

Configuration Example of Surgery Assistance System

Figure 1:
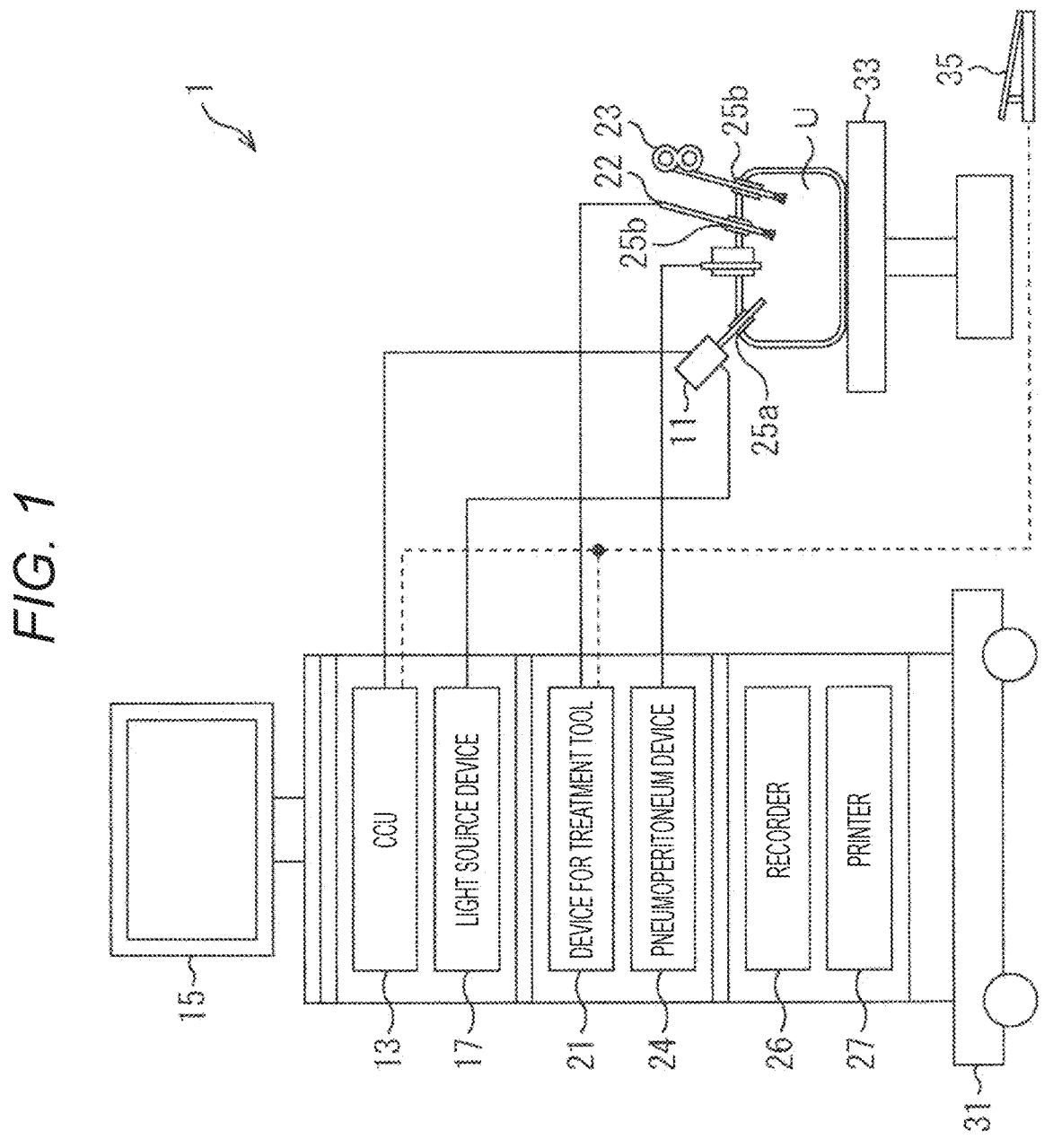
FIG. 1 illustrates a configuration example of a surgery assistance system according to an embodiment of the present disclosure.

FIG. 1 illustrates a configuration example of a surgery assistance system according to an embodiment of the present disclosure.

FIG. 1 illustrates an example of an endoscopic surgery system that is used, for example, in endoscopic surgery of the abdomen that is performed instead of laparotomy in the related art at a medical site.

In a surgery assistance system 1 illustrated in FIG. 1, in endoscopic surgery of the abdomen, a plurality of perforating tools called trocars 25a and 25b are attached through the abdominal wall instead of cutting the abdominal wall and performing laparotomy, as in the related art. Then, a laparoscope (hereinafter also referred to as an endoscope or imager) 11 serving as medical equipment for observation that observes the inside of a patient's body, an energy treatment tool 22, forceps 23, and the like are inserted into the body through holes provided in the trocars 25a and 25b.

An operator performs treatment, such as the excision of an affected part (e.g. a tumor) U inside the patient's body by using the energy treatment tool 22 and the like, while viewing, in real time, an image of the affected part U that has been captured by performing video imaging using the endoscope 11. The endoscope 11, the energy treatment tool 22, and the forceps 23 are held by an operator, a robot, or the like. Note that the operator refers to a healthcare worker who is involved in surgery performed in an operating room, and the operator includes, for example, a doctor who is monitoring the surgery in a place that is different from the operating room, and the like in addition to a surgeon, an assistant, an endoscopist, and a nurse of the surgery.

In an operating room in which endoscopic surgery, as described above, is performed, a cart 31 on which devices and the like for the endoscopic surgery are mounted, a patient bed 33 on which a patient lies, a foot switch 35, and the like are disposed. In the cart 31, a camera control unit (CCU) 13, a light source device 17, a device for a treatment tool 21, a pneumoperitoneum device 24, a display device 15, a recorder 26, a printer 27, and the like are placed, for example, as medical equipment.

An image signal that has been obtained by imaging the affected part U using an observation optical system of the endoscope 11 is transmitted to the CCU 13 via a camera cable. The CCU 13 may be connected to the endoscope 11 via the camera cable, or may be connected to the endoscope 11 via a radio communication path. The CCU 13 performs signal processing on the image signal that has been output from the endoscope 11, and outputs an image signal after signal processing to the display device 15. By employing the configuration described above, an endoscopic image of the affected part U is displayed on the display device 15.

Note that the CCU 13 may output the image signal after signal processing to the recorder 26 so as to cause the recorder 26 to record the endoscopic image of the affected part U as image data (for example, moving image data). Furthermore, the CCU 13 may output the image signal after signal processing to the printer 27 so as to cause the printer 27 to print the endoscopic image of the affected part U.

The light source device 17 is connected to the endoscope 11 via a light guide cable, and can irradiate the affected part U with rays of light having various wavelengths while switching the rays of light. Light emitted from the light source device 17 may be used, for example, as auxiliary light.

The device for the treatment tool 21 corresponds, for example, to a high-frequency output device that outputs a high-frequency current to the energy treatment tool 22 that cuts off the affected part U by using electric heat.

The pneumoperitoneum device 24 includes an air feeding unit and an air-intake unit, and feeds air, for example, to an abdominal region inside a patient's body (surgical subject).

The foot switch 35 controls the CCU 13, the device for the treatment tool 21, and the like by using a foot operation of an operator, an assistant, or the like as a trigger signal.

(Display of Annotation)

The surgery assistance system according to this embodiment realizes the writing of an annotation to the surface of an organ or a body cavity photographed in an endoscopic image (hereinafter referred to as an operative field image) that has been captured by the endoscope 11. The annotation described above refers to visual information that an operator uses so as to present a region to be operated, such as a physical region of the surgical subject and the like, to another operator, without obscuring a view by the another operator of the operative field image.

Figure 2:
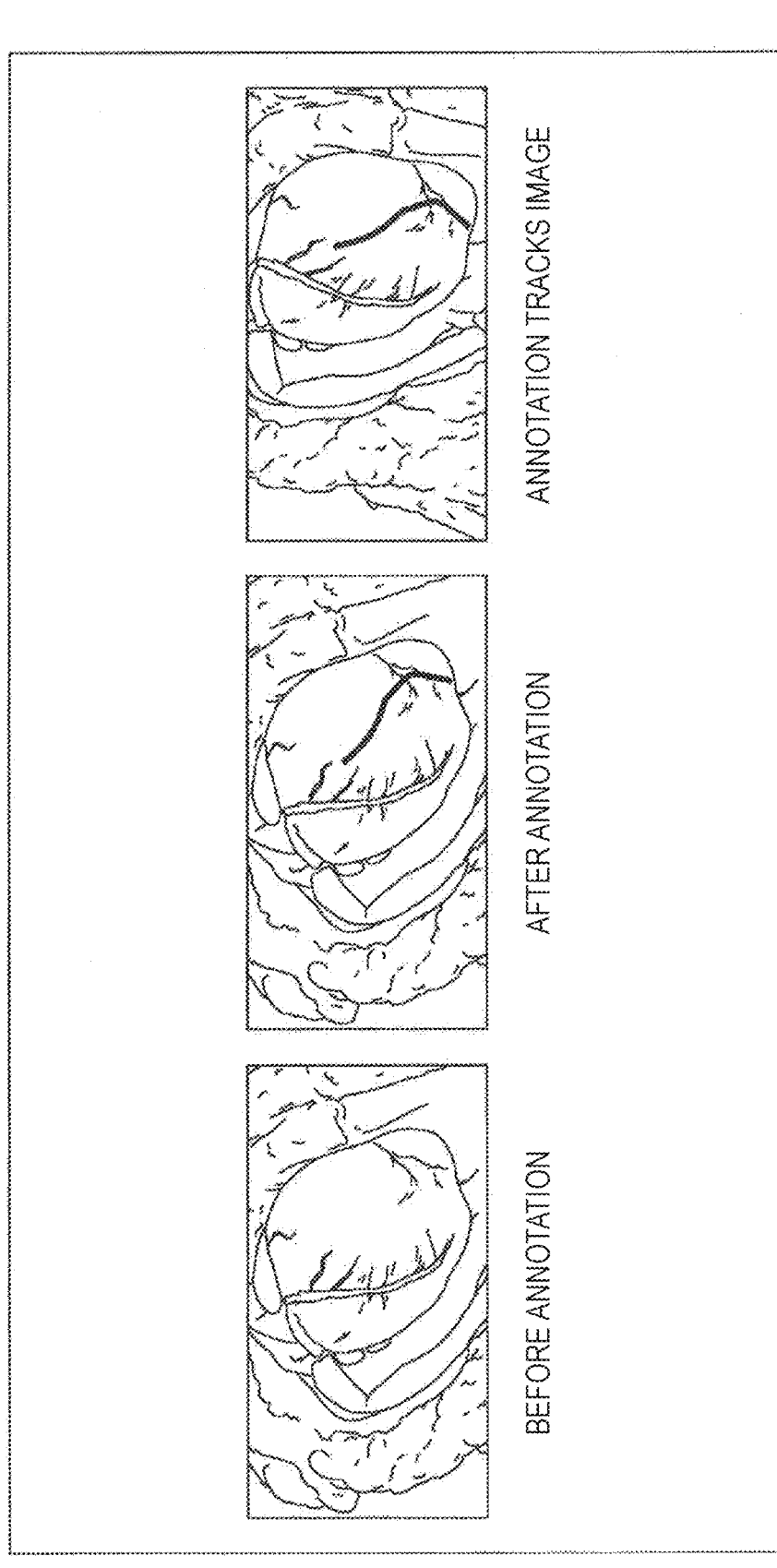
FIG. 2 is a diagram explaining a display of an annotation.

Specifically, when a first user (an operator) specifies a position in which the first user desires to write an annotation on the surface of an organ that is photographed in an operative field image illustrated in a left-hand portion of FIG. 2, a linear annotation is superimposed onto the position (a specified position) that has been specified by the first user on the operative field image, as illustrated in the center of FIG. 2.

Even in a case where the position or posture of the endoscope 11 changes, the written annotation is displayed while tracking the specified position on the operative field image, as illustrated in a right-hand portion of in FIG. 2.

In the surgery assistance system according to this embodiment, the position (the specified position) of an annotation is retained on the basis of a visual and stereoscopic texture of the surface of an organ or a body cavity photographed in an operative field image and a positional relationship of the surface of the organ or the body cavity, and the orientation and position (the movement) of the endoscope 11 are estimated. Then, a display position is updated on the basis of a result of estimating the movement in such a way that the annotation stays superimposed in the same position on the organ (an estimated region of the second operation field image that corresponds to the physical region of the surgical subject).

The position (the specified position) of an annotation is fixed regardless of coordinates on a screen on which an operative field image is displayed. Therefore, even in a case where an annotation is written to a still image obtained by stopping the operative field image or a past operative field image that has been recorded, a result of writing the annotation is reflected in a currently displayed operative field image.

(Functional Configuration Example of Surgery Assistance System)

Figure 3:
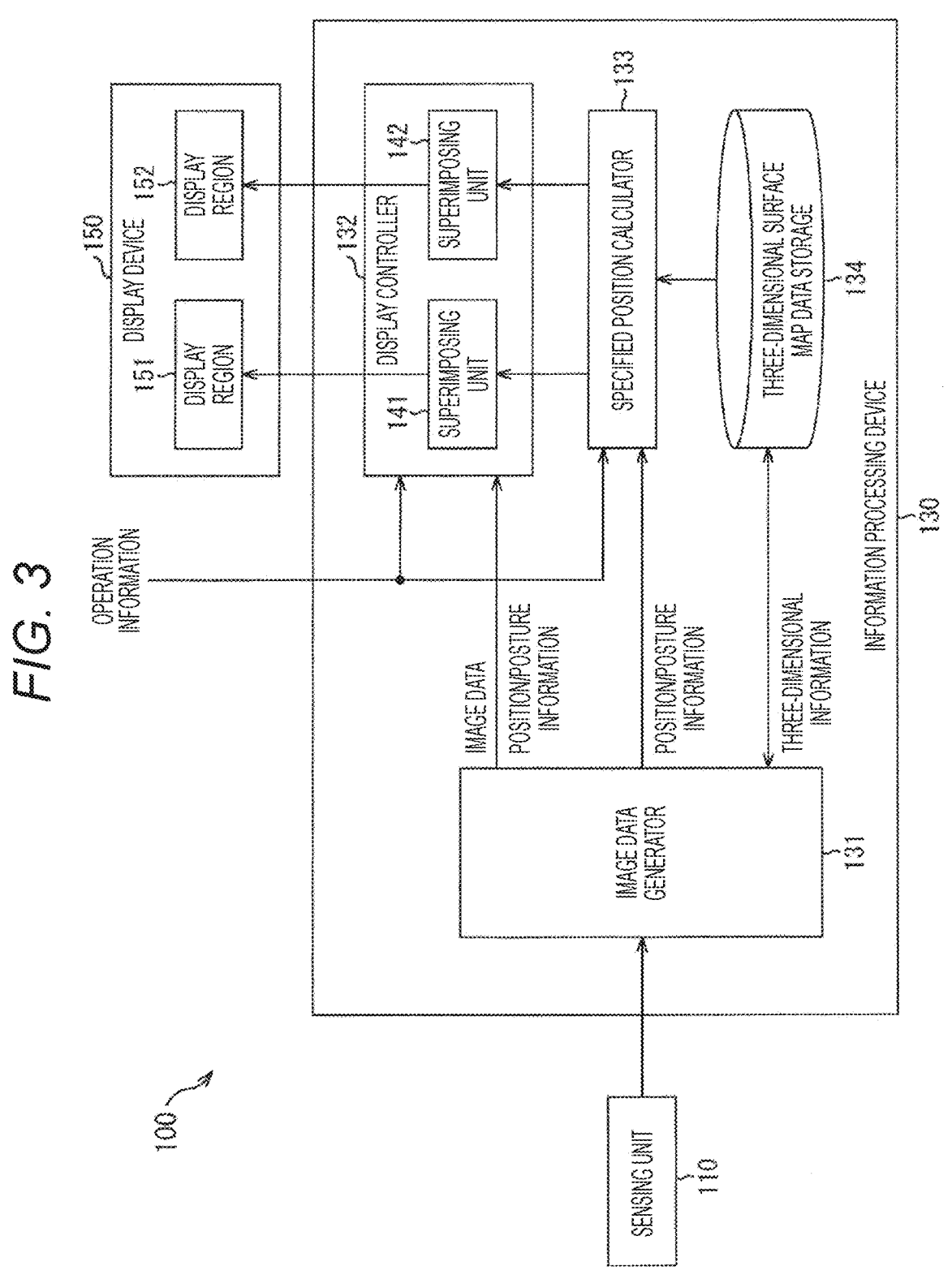
FIG. 3 is a block diagram illustrating a functional configuration example of a surgery assistance system.

FIG. 3 is a block diagram illustrating a functional configuration example of a surgery assistance system that is capable of realizing the display described above of an annotation.

A surgery assistance system 100 illustrated in FIG. 3 is configured by a sensing unit 110, an information processing device 130, and a display device 150.

The sensing unit 110 corresponds to the endoscope 11 of FIG. 1, and provides an image signal obtained by performing imaging to the information processing device 130.

The information processing device 130 corresponds to the CCU 13 of FIG. 1, and the information processing device 130 performs signal processing on the image signal obtained from the sensing unit 110, and provides the image signal to the display device 150.

The display device 150 corresponds to the display device 15 of FIG. 1, and displays an operative field image on the basis of the image signal obtained from the information processing device 130. Details will be described later, but the display device 150 is provided with two display regions (a first display region 151 and a second display region 152), and one operative field image is displayed in each of the two display regions.

The information processing device 130 includes an image data generator 131, a display controller 132, a specified position calculator 133, and a three-dimensional surface map data storage 134.

The image data generator 131 performs development processing on the image signal obtained from the sensing unit 110 so as to provide image data of an operative field image including a plurality of frames to the display controller 132.

Furthermore, the image data generator 131 estimates the movement of the endoscope 11 on the basis of each of the frames that configure the operative field image so as to generate position/posture information indicating the movement, and provides the position/posture information to the display controller 132 and the specified position calculator 133.

Moreover, the image data generator 131 generates three-dimensional information indicating a three-dimensional structure of a subject (an organ or an inside of a body cavity) that is photographed in the operative field image on the basis of each of the frames that configure the operative field image and the estimated movement of the endoscope 11. The generated three-dimensional information is stored as three-dimensional surface map data in the three-dimensional surface map data storage 134.

The detailed configurations of the sensing unit 110 and the image data generator 131 will be described later.

The display controller 132 performs control to display an operative field image in each of the two display regions (the first display region 151 and the second display region 152) of the display device 150 on the basis of the image data obtained from the image data generator 131.

The display controller 132 includes a first superimposing unit 141 and a second superimposing unit 142.

The first superimposing unit 141 superimposes an annotation onto a position (a specified position) specified by a user on an operative field image displayed in the first display region 151. Specifically, the first superimposing unit 141 obtains a specified position on the operative field image displayed in the first display region 151 on the basis of the position/posture information obtained from the image data generator 131 and a specified position calculated by the specified position calculator 133, and the first superimposing unit 141 superimposes an annotation. The specified position corresponds to a physical region of the surgical subject.

On the other hand, the second superimposing unit 142 superimposes an annotation while tracking a specified position on an operative field image that is displayed in the second display region 152. Specifically, the second superimposing unit 142 obtains a specified position on the operative field image displayed in the second display region 152 on the basis of the position/posture information obtained from the image data generator 131 and the specified position calculated by the specified position calculator 133, and the second superimposing unit 142 superimposes an annotation on an estimated region that corresponds to the physical region of the surgical subject.

When the specified position calculator 133 obtains information indicating the writing of an annotation to the operative field image displayed in the first display region 151 as operation information indicating the user's operation, the specified position calculator 133 calculates a specified position on the basis of the position/posture information obtained from the image data generator 131 and the three-dimensional surface map data of the three-dimensional surface map data storage 134.

Specifically, the specified position calculator 133 obtains which position on the three-dimensional surface map data a position in which an annotation has been written corresponds to, on the basis of a current position and a current posture of the endoscope 11 that are indicated by the position/posture information. The specified position that has been obtained as described above is retained in the specified position calculator 133, and is provided to the first superimposing unit 141 and the second superimposing unit 142.

Detailed Configuration Examples 1 of Sensing Unit and Image Data Generator

Here, detailed configuration examples of the sensing unit 110 and the image data generator 131 are described with reference to FIG. 4.

The sensing unit 110 includes an image sensor 211, and provides an image signal obtained by performing imaging to the information processing device 130.

The image data generator 131 is configured by a development processing unit 221, an initial three-dimensional data generator 222, a camera position/posture estimating unit 223, and a three-dimensional surface restoring unit 224.

The development processing unit 221 performs development processing on an image signal obtained from the image sensor 211 so as to generate image data. The generated image data is provided to each of the initial three-dimensional data generator 222, the camera position/posture estimating unit 223, and the three-dimensional surface restoring unit 224.

The initial three-dimensional data generator 222 obtains three-dimensional information indicating a three-dimensional structure of a subject on the basis of a correspondence relationship among pixel positions in which a texture of the surface of an organ is identical in respective pieces of image data (frame data) that are provided in time series from the development processing unit 221. As the texture, a pixel value of image data is used with no change, or a feature amount extracted from the image data is used. The initial three-dimensional data generator 222 generates initial three-dimensional surface map data by using the obtained three-dimensional information.

The camera position/posture estimating unit 223 estimates a camera position/posture (estimates the movement of the endoscope 11) on the basis of a correspondence relationship between a pixel value or a feature amount of each of the pieces of image data (frame data) that are provided in time series from the development processing unit 221 and a pixel value or a feature amount of temporally preceding image data. The camera position/posture estimating unit 223 generates position/posture information indicating the movement of the endoscope 11 on the basis of a result of estimating the movement.

The three-dimensional surface restoring unit 224 restores three-dimensional information based on the pixel value or the feature amount of the image data from the movement of the endoscope 11 that has been estimated by the camera position/posture estimating unit 223, and updates the three-dimensional surface map data that has been generated by the initial three-dimensional data generator 222. The updated three-dimensional surface map data is stored in the three-dimensional surface map data storage 134. Furthermore, the three-dimensional surface restoring unit 224 may read, as the three-dimensional information, the three-dimensional surface map data stored in the three-dimensional surface map data storage 134, and may update the three-dimensional surface map data.

A simultaneous localization and mapping (SLAM) technique can be used to generate the three-dimensional surface map data and estimate the camera position/posture, as described above. A basic principle of a SLAM technique using a monocular camera is described, for example, in Andrew J. Davison, "Real-Time Simultaneous Localization and Mapping with a Single Camera", Proceedings of the 9th IEEE International Conference on Computer Vision Volume 2, 2003, pp. 1403-1410. Note that a SLAM technique for visually estimating a position by using a camera image is also particularly referred to as visual SLAM.

Detailed Configuration Examples 2 of Sensing Unit and Image Data Generator

Figure 5:
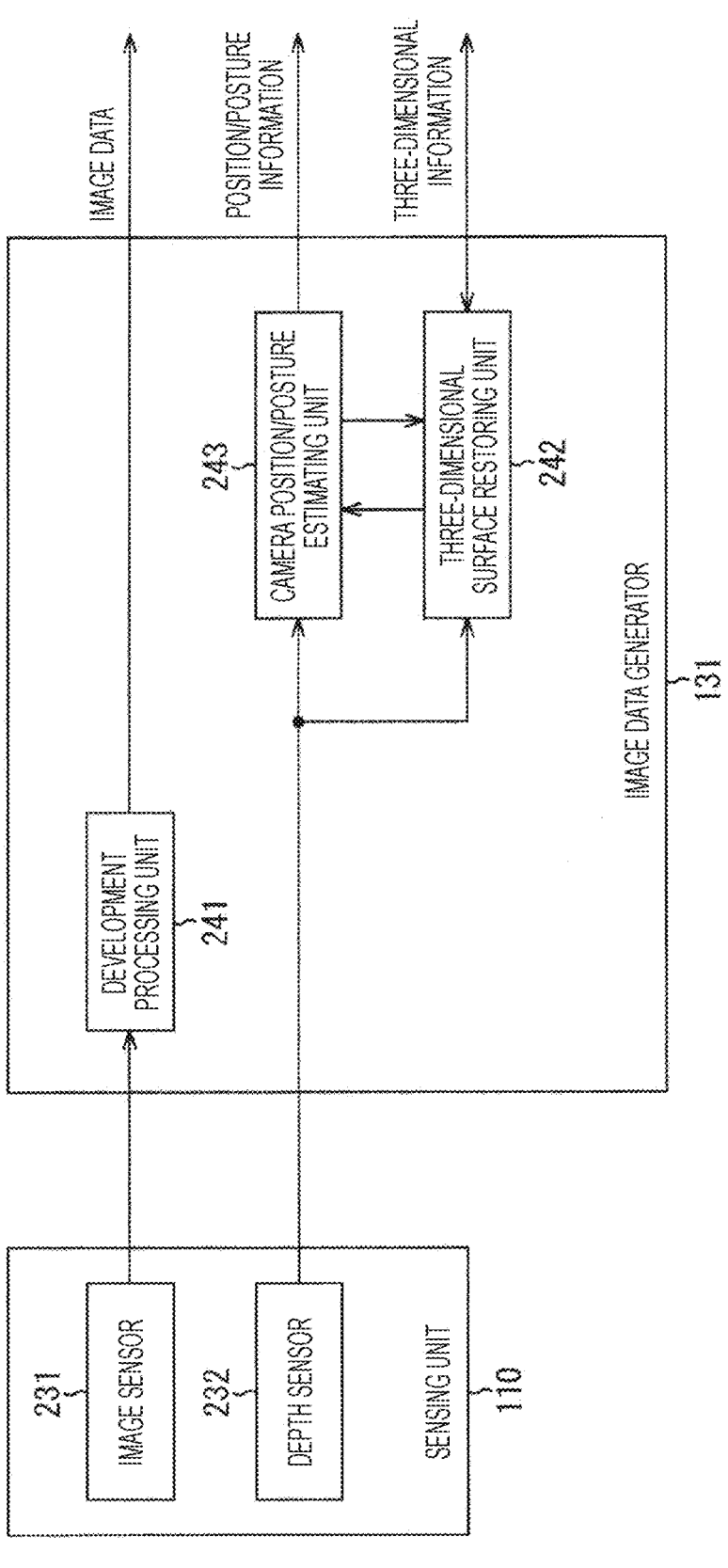
FIG. 5 is a block diagram illustrating detailed configuration examples of a sensing unit and an image data generator.

The sensing unit 110 and the image data generator 131 can also employ the configurations illustrated in FIG. 5.

The sensing unit 110 of FIG. 5 includes a depth sensor 232 in addition to an image sensor 231, and provides depth data of an imaging range together with an image signal obtained by performing imaging to the image data generator 131.

The image data generator 131 of FIG. 5 is configured by a development processing unit 241, a three-dimensional surface restoring unit 242, and a camera position/posture estimating unit 243.

The development processing unit 241 performs development processing on an image signal obtained from the image sensor 231 so as to generate image data.

The three-dimensional surface restoring unit 242 generates three-dimensional surface map data by obtaining three-dimensional information relating to a subject from depth data obtained from the depth sensor 232, or updates the three-dimensional surface map data by performing alignment in a three-dimensional space.

The camera position/posture estimating unit 243 compares depth data that is currently obtained from the depth sensor 232 with the three-dimensional surface map data that has been generated or restored by the three-dimensional surface restoring unit 242 so as to estimate a camera position/posture (estimate the movement of the endoscope 11).

In the configuration of FIG. 5, the movement of the endoscope 11 is estimated, and this results in a reduction in a space that the three-dimensional surface restoring unit 242 searches in order to perform alignment in a three-dimensional space.

Detailed Configuration Examples 3 of Sensing Unit and Image Data Generator

Figure 6:
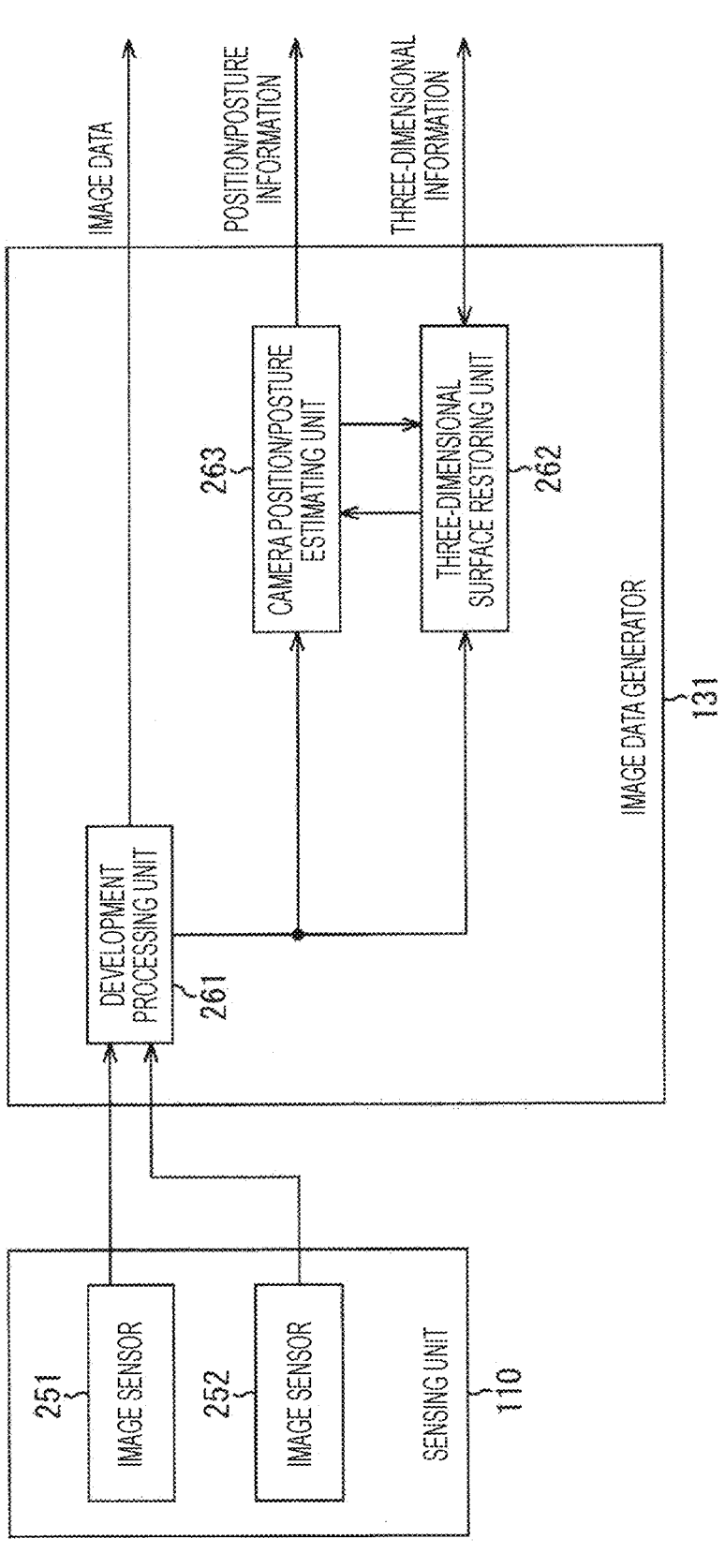
FIG. 6 is a block diagram illustrating detailed configuration examples of a sensing unit and an image data generator.

The sensing unit 110 and the image data generator 131 can also employ the configurations illustrated in FIG. 6.

The sensing unit 110 of FIG. 6 is configured as a stereo camera, includes a pair of image sensors 251 and 252, and provides each of the image signals obtained by performing imaging to the image data generator 131.

The image data generator 131 of FIG. 6 is configured by a development processing unit 261, a three-dimensional surface restoring unit 262, and a camera position/posture estimating unit 263.

The development processing unit 261 performs development processing on an image signal obtained from the image sensor 251 so as to generate image data.

Furthermore, the development processing unit 261 performs parallax-based triangulation using image signals obtained from the image sensors 251 and 252 so as to generate depth data of an imaging range, and provides the depth data to the three-dimensional surface restoring unit 262 and the camera position/posture estimating unit 263.

The three-dimensional surface restoring unit 262 generates three-dimensional surface map data by obtaining three-dimensional information relating to a subject from the depth data obtained from the development processing unit 261, or updates the three-dimensional surface map data by performing alignment in a three-dimensional space.

The camera position/posture estimating unit 263 compares depth data that is currently obtained from the development processing unit 261 with the three-dimensional surface map data that has been generated or restored by the three-dimensional surface restoring unit 262 so as to estimate a camera position/posture (estimate the movement of the endoscope 11).

By employing the surgery assistance system 100 configured as described above, an annotation written to an operative field image is displayed in such a way that the annotation stays in a position in which the annotation has been initially written, even in a case where the endoscope 11 has moved.

(Interpolation of Three-Dimensional Information)

In the surgery assistance system 100, when a user writes an annotation, in a case where the three-dimensional surface map data has a low density and there is no three-dimensional information that corresponds to a position (a specified position) in which the annotation will be superimposed, the three-dimensional information may be interpolated.

For example, three-dimensional information relating to the specified position is estimated by using three-dimensional information that corresponds to points around the specified position in the three-dimensional surface map data.

Figure 4:
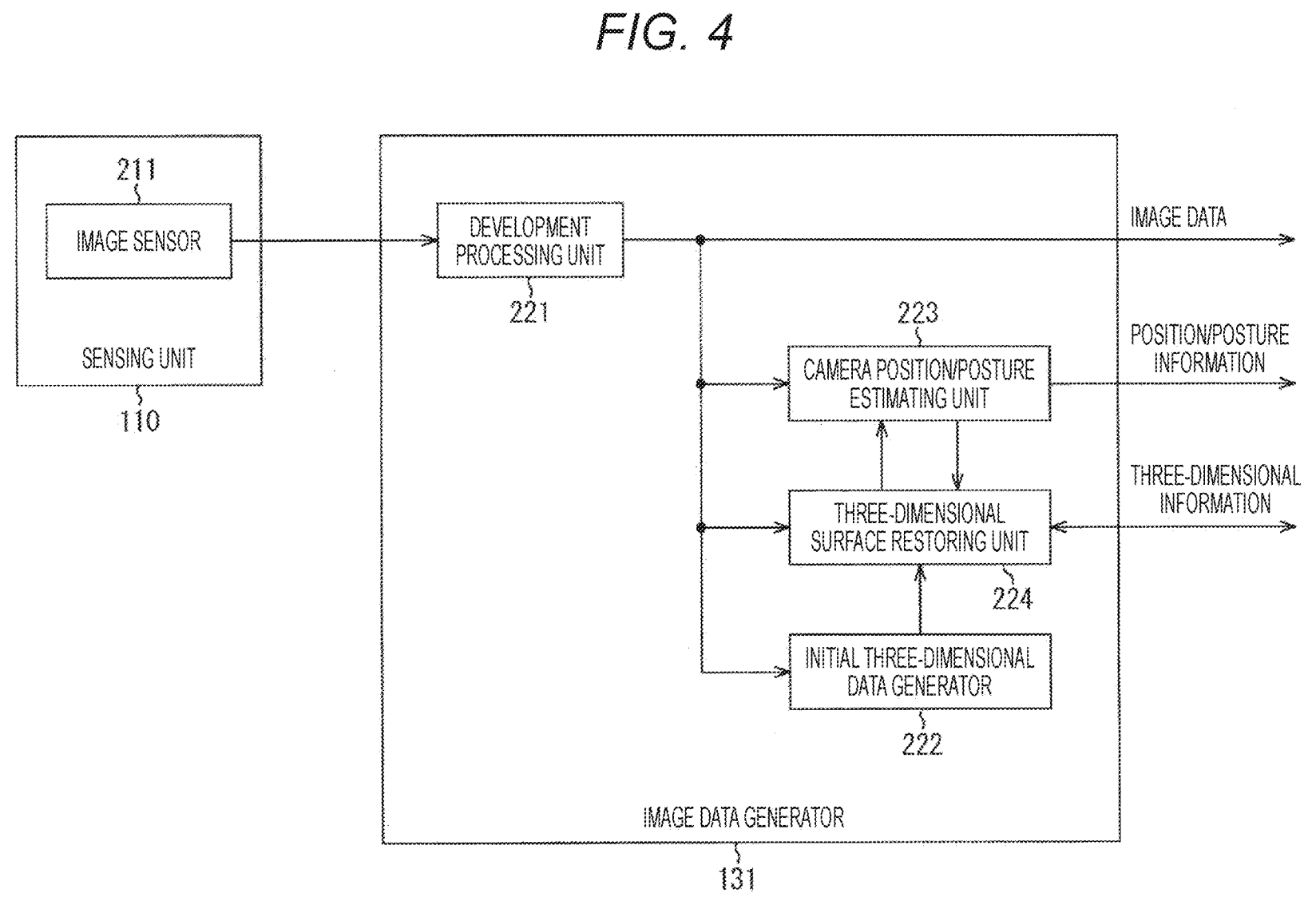

Furthermore, in a case where the surgery assistance system 100 has the configuration of FIG. 4, three-dimensional surface map data having a high density may be obtained according to a multi-view stereo technique by using the camera position/posture estimated by the camera position/posture estimating unit 223 and image data that includes a plurality of frames and that corresponds to the camera position/posture. In this case, the three-dimensional information relating to the specified position can be estimated by using the obtained three-dimensional surface map data having a high density.

(Update of Three-Dimensional Information)

In the surgery assistance system 100, in a case where an object to be observed in a body cavity moves or changes in shape, the position of an annotation can be caused to change according to a change in the object to be observed.

For example, when the three-dimensional surface map data is updated by using three-dimensional information restored by the three-dimensional surface restoring unit 262, in a case where the position of a certain region has significantly changed, three-dimensional information relating to the certain region is updated to the latest three-dimensional information that has been restored.

Moreover, in the three-dimensional surface map data, the reliability of the entirety of the three-dimensional surface map data can be improved by adding time information indicating a generation/update time to three-dimensional information relating to each position. By updating the three-dimensional surface map data in such a way that the latest information having a high reliability is left, even in a case where the object to be observed in the body cavity moves or changes in shape, the annotation can be displayed while tracking the object to be observed.

<2. Flow of Annotation Writing Processing>

Next, the flow of annotation writing processing in the surgery assistance system 100 according to this embodiment is described with reference to the flowcharts of FIGS. 7 and 8.

Figure 7:
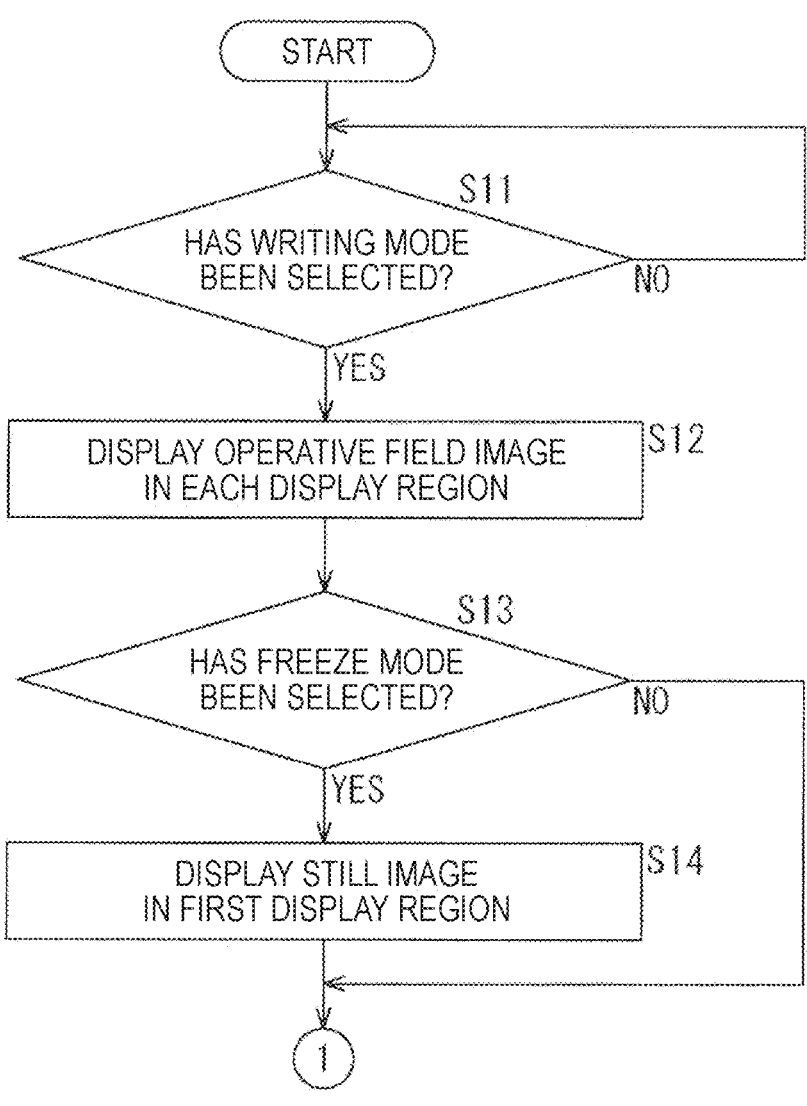
FIG. 7 is a flowchart explaining annotation writing processing.
Figure 8:
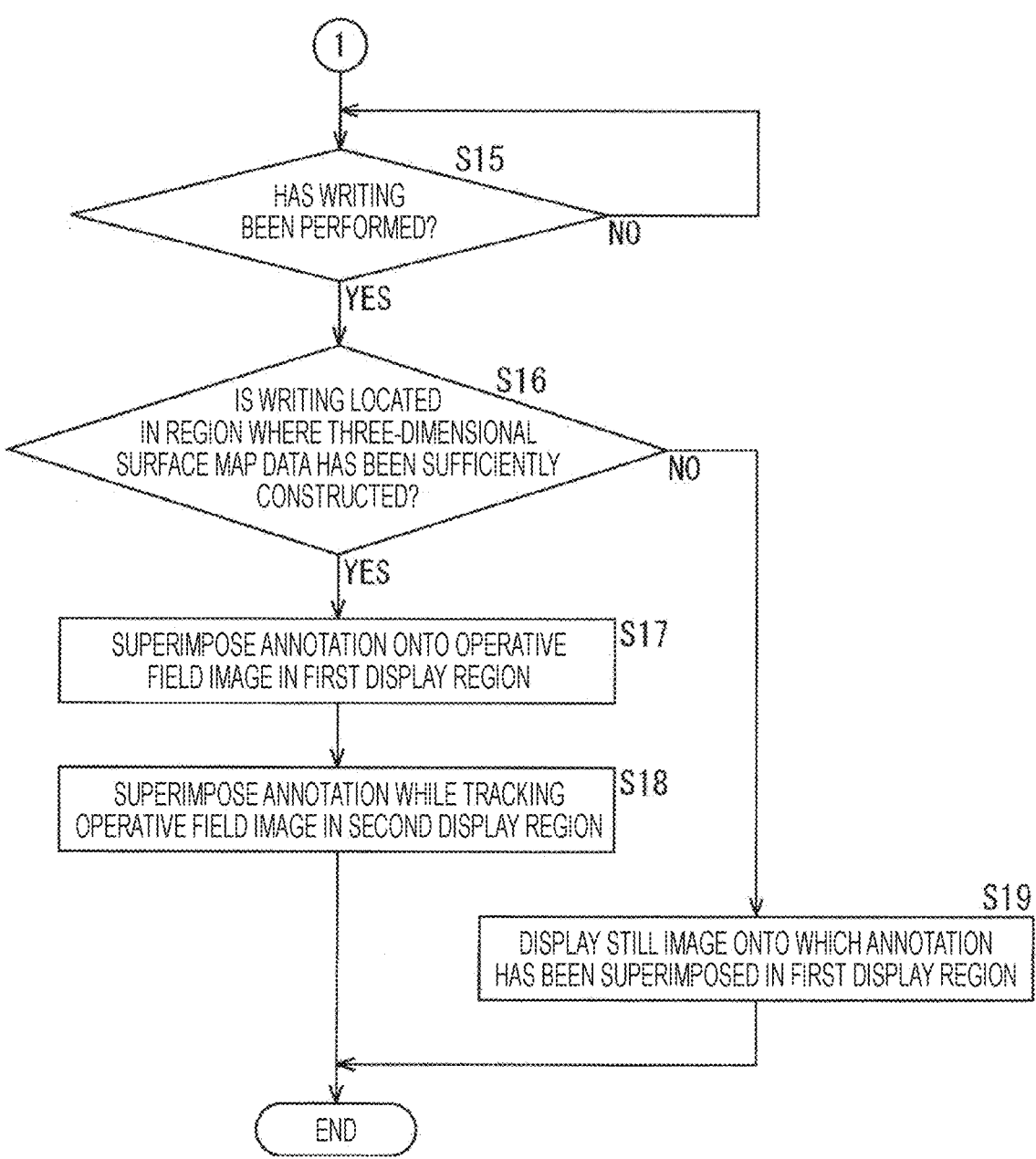
FIG. 8 is a flowchart explaining the annotation writing processing.

The processing of FIGS. 7 and 8 is performed, for example, when an advising doctor presents a region to be operated in order to assist an inexperienced surgeon. In this example, assume that an advising doctor presents a region to be operated by using an operative field image displayed in the first display region 151, and that a surgeon performs surgery while viewing an operative field image displayed in the second display region 152.

In step S11, the display controller 132 determines whether or not a writing mode for enabling an annotation to be written has been selected, on the basis of operation information indicating an operation of a user (specifically, the advising doctor).

Figure 9:
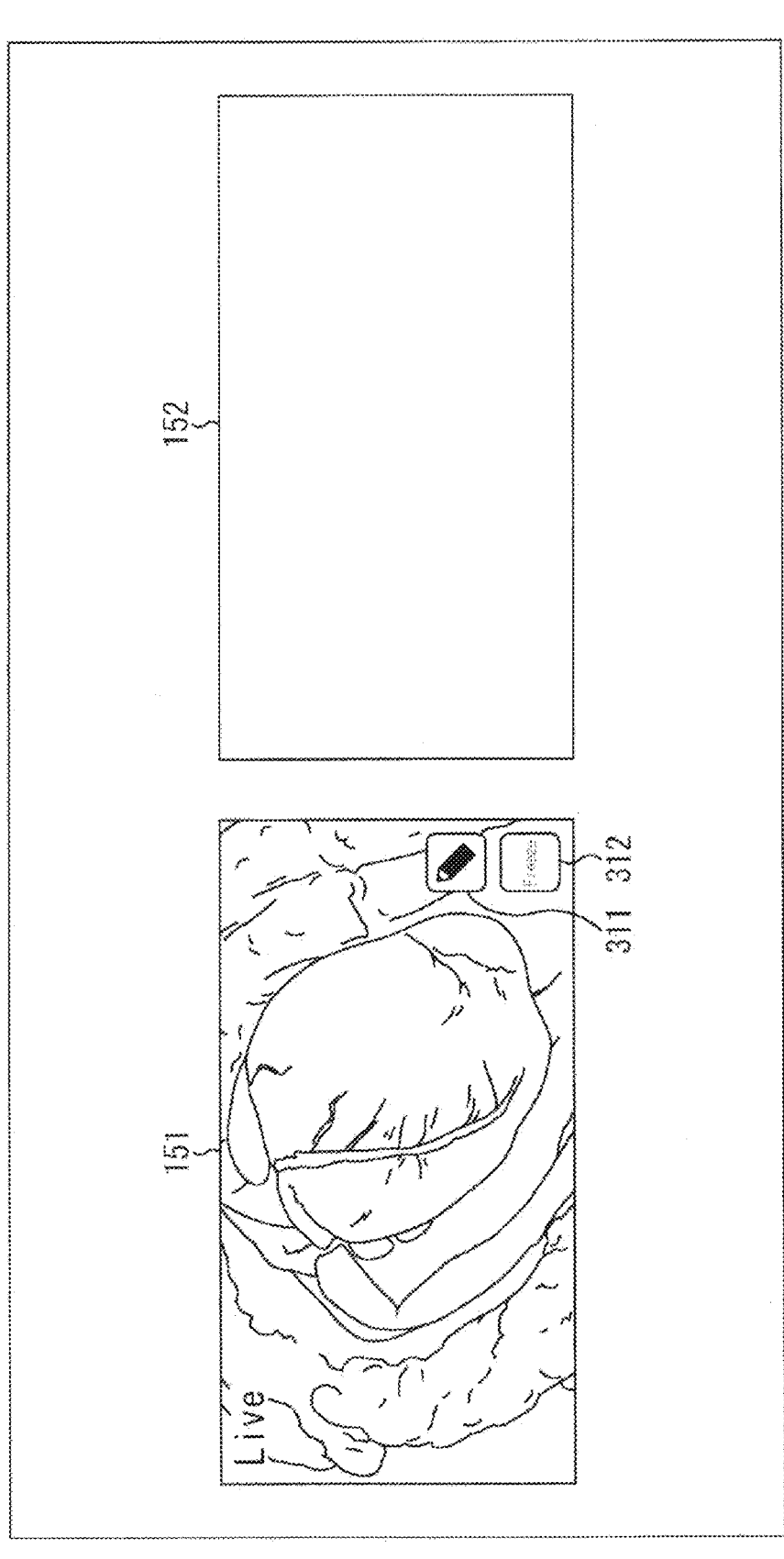
FIG. 9 illustrates a display example of an operative field image in the annotation writing processing.

FIG. 9 illustrates a display example of operative field images that are displayed in the first display region 151 and the second display region 152.

In the first display region 151, an operative field image captured by the sensing unit 110 is displayed in real time, and the characters "Live" indicating this fact are displayed in an upper left-hand portion of a screen of the first display region 151. Note that nothing is displayed in the second display region 152.

A writing mode button 311 and a freeze mode button 312 are displayed in a lower right-hand portion of the first display region 151 having a touch panel function. The advising doctor performs an operation to touch the writing mode button 311 displayed in the first display region 151, so that the writing mode is selected.

In other words, the process of step S11 is repeated until the advising doctor performs the operation to touch the writing mode button 311. When the operation to touch the writing mode button 311 is performed, the processing moves on to step S12.

In step S12, the display controller 132 displays an operative field image in each of the first display region 151 and the second display region 152.

Figure 10:
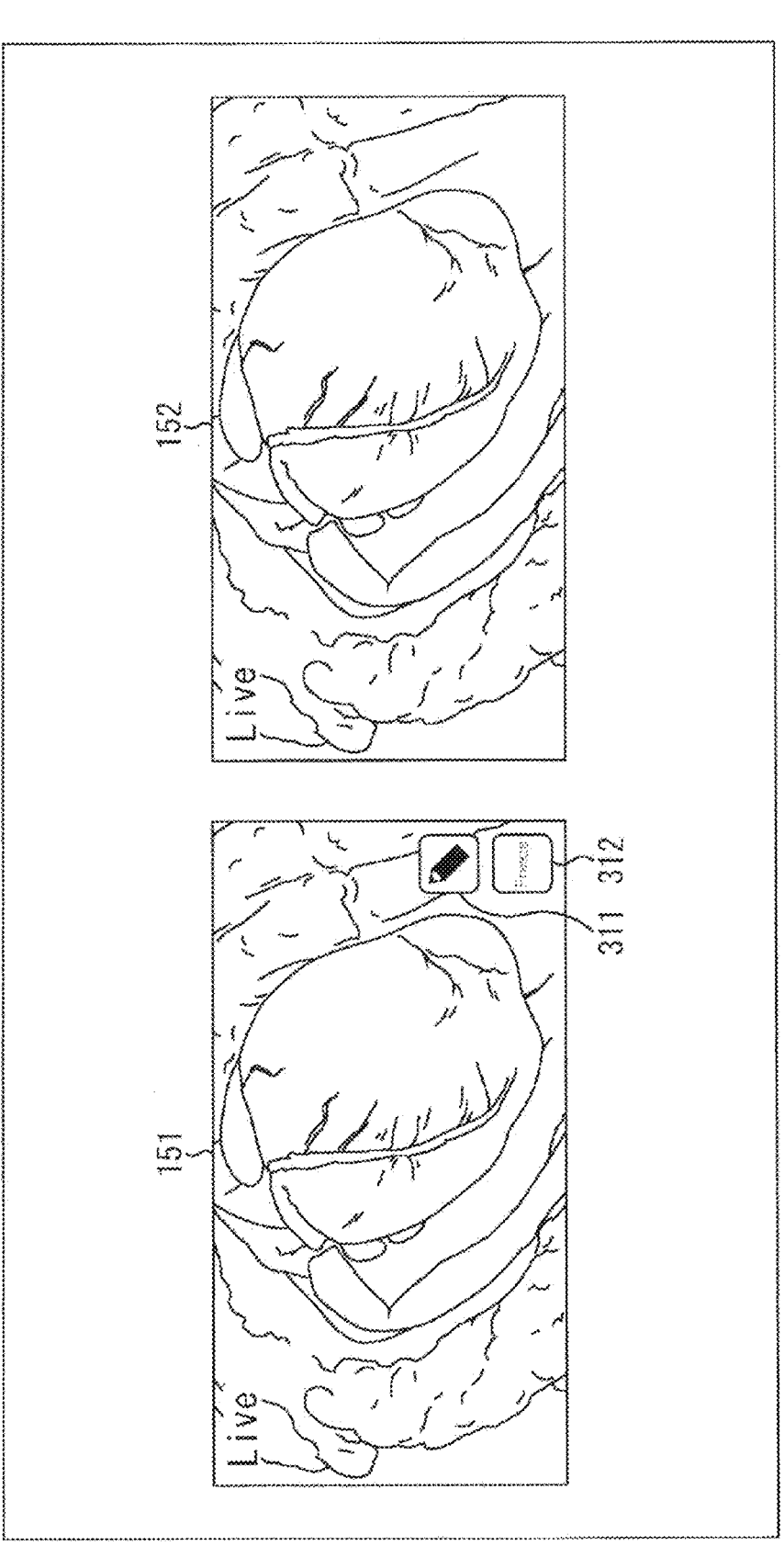
FIG. 10 illustrates a display example of an operative field image in the annotation writing processing.

Specifically, as illustrated in FIG. 10, an operative field image is also displayed in real time in the second display region 152 similarly to the first display region 151, and the characters "Live" indicating this fact are displayed in an upper left-hand portion of a screen of the second display region 152.

In step S13, the display controller 132 determines whether or not a freeze mode for freezing (stopping) a display in the first display region 151 has been selected, on the basis of the operation information indicating the operation of the user (the advising doctor). Specifically, it is determined whether or not the advising doctor has performed an operation to touch the freeze mode button 312 displayed in the first display region 151.

Accordingly, in step S13, when the advising doctor performs the operation to touch the freeze mode button 312, the processing moves on to step S14.

In step S14, the display controller 132 displays a still image that is a single frame of the operative field image that is displayed in real time in the first display region 151 instead of the operative field image.

Figure 11:
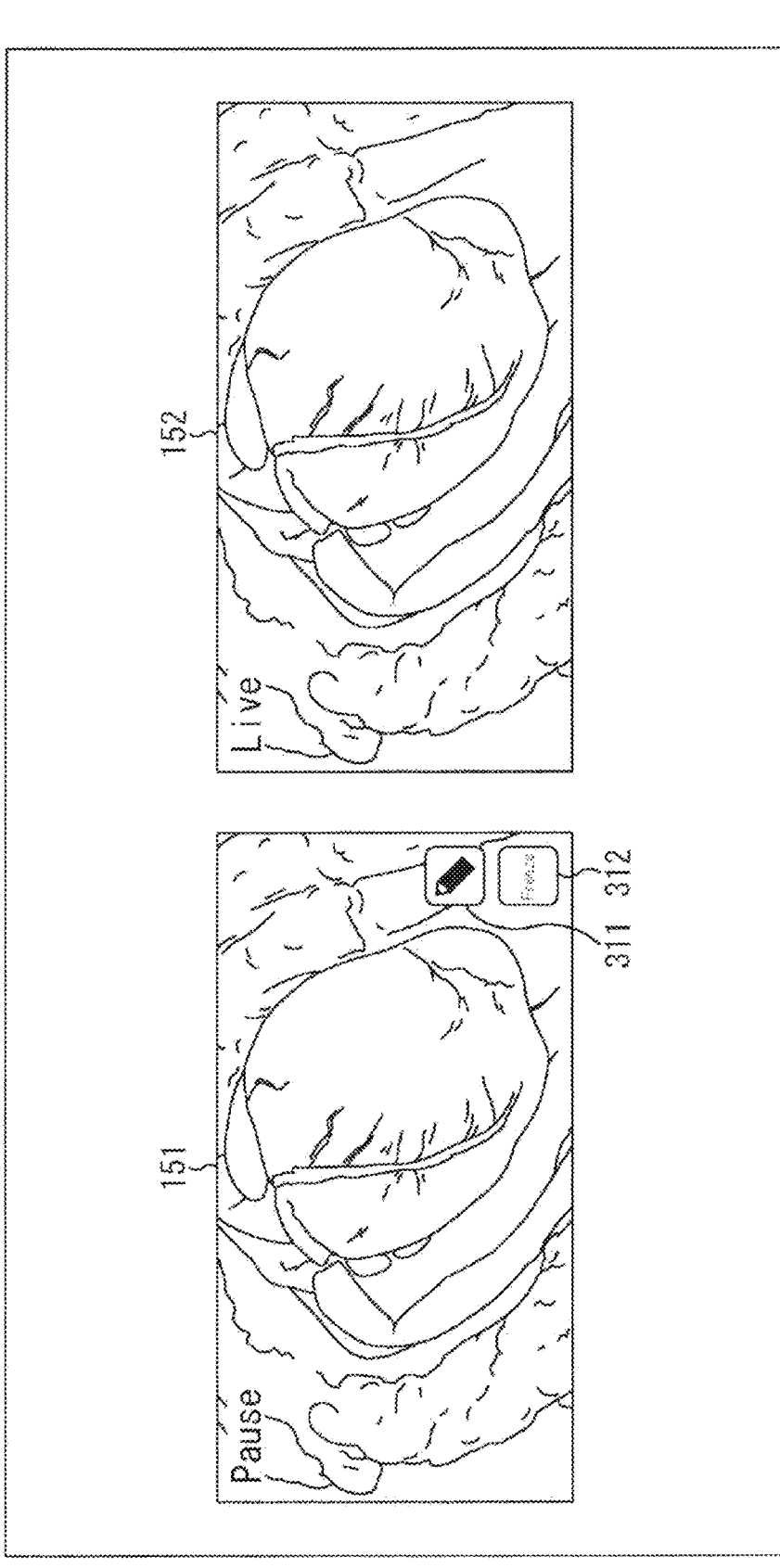
FIG. 11 illustrates a display example of an operative field image in the annotation writing processing.

Specifically, as illustrated in FIG. 11, a single frame at a timing when the operation to touch the freeze mode button 312 is performed of the operative field image is displayed as a still image in the first display region 151. Furthermore, the characters "Pause" indicating that a still image is displayed are displayed in an upper left-hand portion of the screen of the first display region 151. At this time, the display controller 132 retains current position/posture information obtained from the image data generator 131 together with the still image at a timing when the operation to touch the freeze mode button 312 is performed.

In contrast, in step S13, in a case where the advising doctor does not perform the operation to touch the freeze mode button 312, step S14 is skipped.

In step S15, the display controller 132 determines whether or not an annotation has been written to the operative field image displayed in the first display region 151, on the basis of the operation information indicating the operation of the user (the advising doctor). The annotation is written, for example, by the advising doctor performing an operation to trace a region to be operated or another operation on the first display region 151.

Here, in a case where a still image is displayed in the first display region 151, the writing of the annotation to the still image is accepted. In contrast, in a case where an operative field image (a moving image) displayed in real time is displayed in the first display region 151, the writing of the annotation to the moving image is accepted.

The process of step S15 is repeated until the annotation has been written. When the annotation is written, the processing moves on to step S16.

At this time, in response to the writing of the annotation, the specified position calculator 133 calculates a specified position on the basis of the position/posture information obtained from the image data generator 131 and the three-dimensional surface map data stored in the three-dimensional surface map data storage 134.

In step S16, the display controller 132 determines whether or not a position (the specified position) in which the annotation has been written is located in a region in which the three-dimensional surface map data has been sufficiently constructed.

In step S16, in a case where it is determined that the position in which the annotation has been written is located in a region in which the three-dimensional surface map data has been sufficiently constructed, the processing moves on to step S17.

In step S17, the first superimposing unit 141 superimposes an annotation onto the specified position on the operative field image displayed in the first display region 151.

Then, in step S18, the second superimposing unit 142 superimposes an annotation while tracking the specified position on an operative field image that is displayed in the second display region 152.

Figure 12:
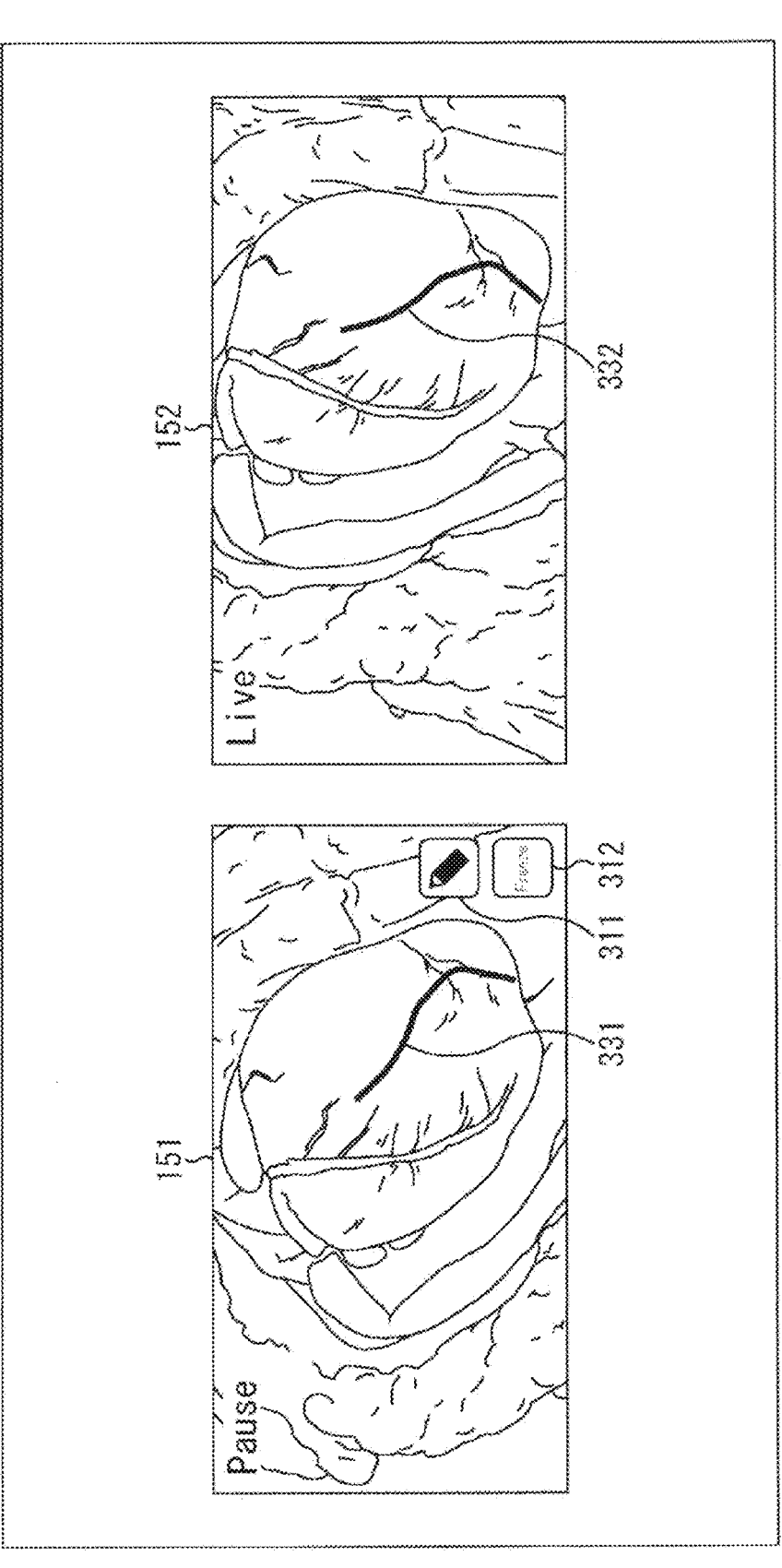
FIG. 12 illustrates a display example of an operative field image in the annotation writing processing.

For example, in a case where the freeze mode has been selected, an annotation 331 is superimposed onto the specified position calculated by the specified position calculator 133 on a still image displayed in the first display region 151, as illustrated in FIG. 12.

On the other hand, an annotation 332 that is similar to the annotation 331 is superimposed onto the specified position on an operative field image that is displayed in real time in the second display region 152 while tracking the specified position on the basis of the position/posture information obtained from the image data generator 131.

In the example of FIG. 12, in an operative field image displayed in the second display region 152, the position and posture of the endoscope 11 have changed from a state where a still image is displayed in the first display region 151, and the position and orientation of an organ photographed in the image have changed. Even in this case, the annotation 332 is displayed while tracking the specified position on the operative field image that is displayed in the second display region 152.

Figure 13:
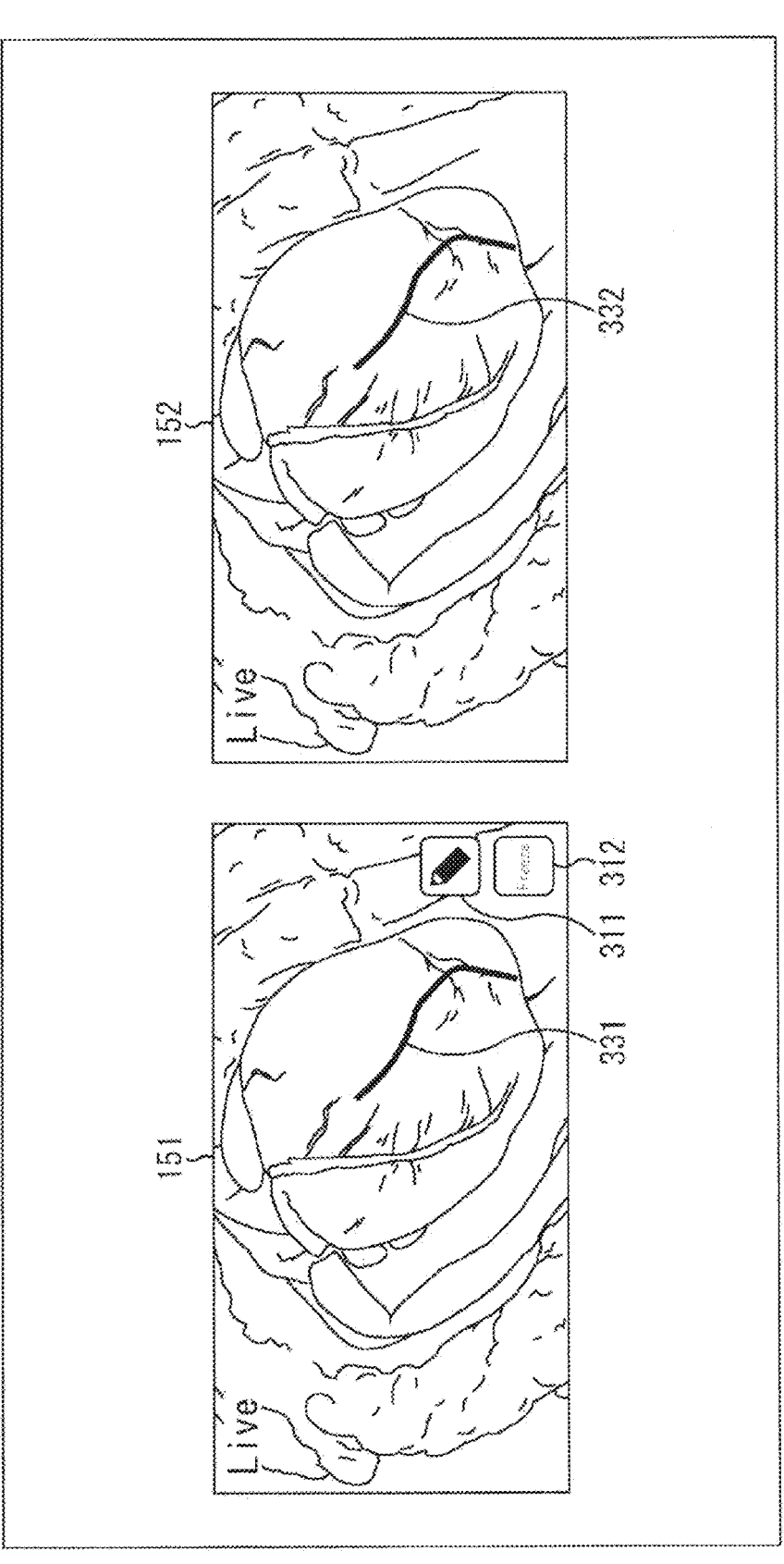
FIG. 13 illustrates a display example of an operative field image in the annotation writing processing.

Furthermore, in a case where the freeze mode has not been selected, the annotation 331 is superimposed onto the specified position calculated by the specified position calculator 133 on an operative field image that is displayed in real time in the first display region 151, as illustrated in FIG. 13.

Similarly, the annotation 332 that is similar to the annotation 331 is superimposed onto the specified position on an operative field image that is displayed in real time in the second display region 152 while tracking the specified position on the basis of the position/posture information obtained from the image data generator 131.

Return now to step S16. In a case where it is determined that the position in which the annotation has been written is not located in a region in which the three-dimensional surface map data has been sufficiently constructed, the processing moves on to step S19.

In step S19, the display controller 132 displays a still image onto which the annotation has been superimposed in the first display region 151.

Figure 14:
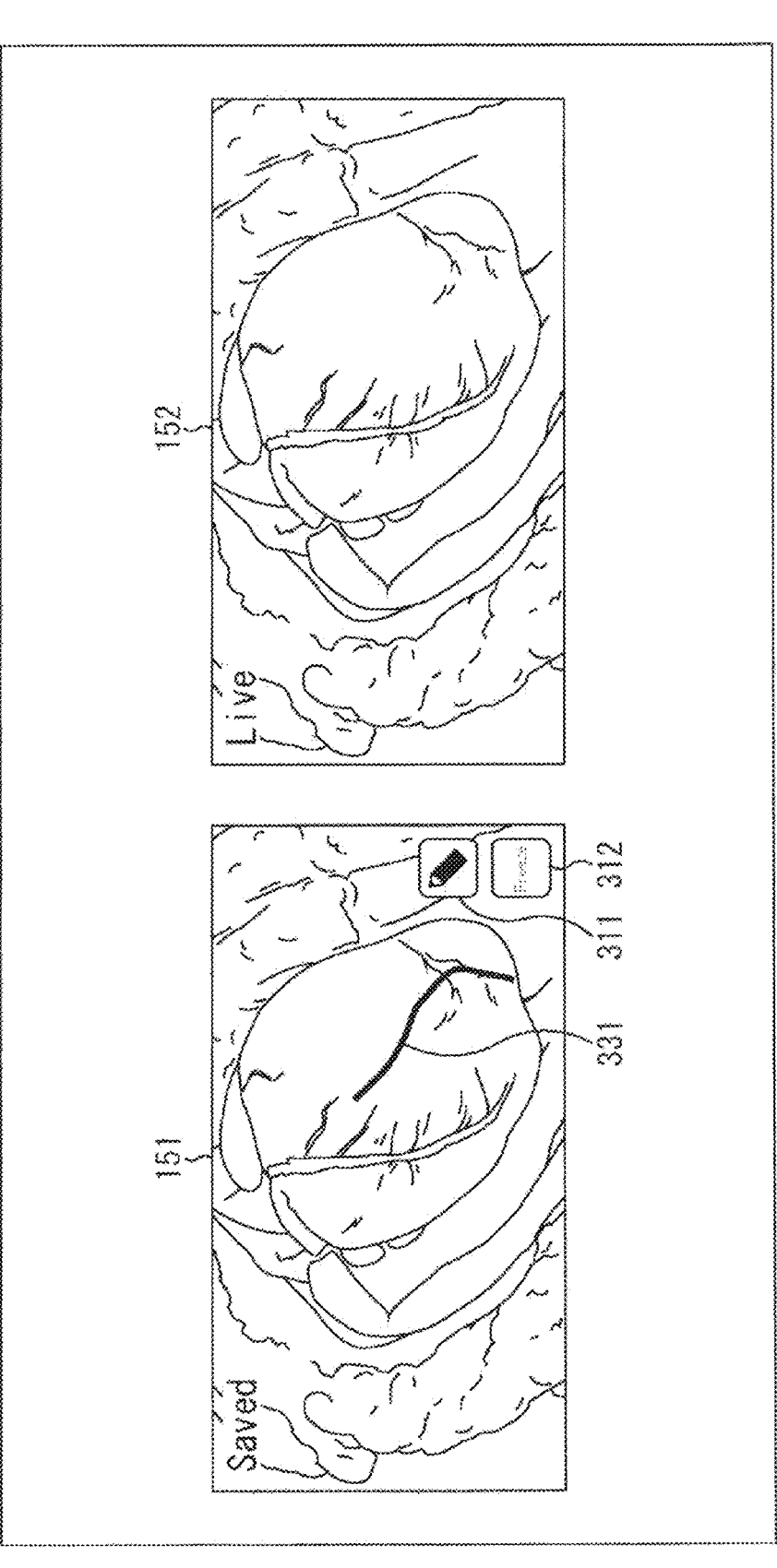
FIG. 14 illustrates a display example of an operative field image in the annotation writing processing.

Specifically, as illustrated in FIG. 14, in a case where the freeze mode has been selected, the first superimposing unit 141 superimposes the annotation 331 onto the specified position on the still image displayed in the first display region 151.

In contrast, in a case where the freeze mode has not been selected, the display controller 132 displays, as a still image, a single frame at a timing when the annotation is written instead of the operative field image displayed in the first display region 151. Then, the first superimposing unit 141 superimposes the annotation 331 onto the specified position on the still image displayed in the first display region 151.

At this time, the characters "Saved" indicating that a still image onto which the annotation 331 has been superimposed is retained are displayed in an upper left-hand portion of the first display region 151.

On the other hand, the second superimposing unit 142 does not superimpose an annotation onto the operative field image displayed in the second display region 152 regardless of whether or not the freeze mode has been selected.

In a case where the three-dimensional surface map data has not been sufficiently constructed in a region in which an annotation has been written, the tracking accuracy of the annotation may be reduced. In view of this, by only displaying a still image at the time of the writing of the annotation without reflecting the annotation in an operative field image displayed in real time, safety can be secured without reducing the usability of the surgeon.

In the processing described above, the writing performed by the advising doctor of an annotation to an operative field image displayed in the first display region 151 is reflected in an operative field image that is displayed in the second display region 152 and that the surgeon is viewing. Accordingly, a motion of the advising doctor to write an annotation to an operative field image does not disturb the surgeon who performs surgery while confirming an operative field image, and communication between operators can be improved.

In particular, in the freeze mode, the advising doctor can freeze an operative field image in order to easily write an annotation, and can cause the written annotation to be reflected in an operative field image that the surgeon is viewing. In other words, the advising doctor can write an annotation in a more accurate position, and the surgeon can continuously observe an operative field image in which the annotation has been reflected while correctly understanding an instruction of the advising doctor.

Figure 15:
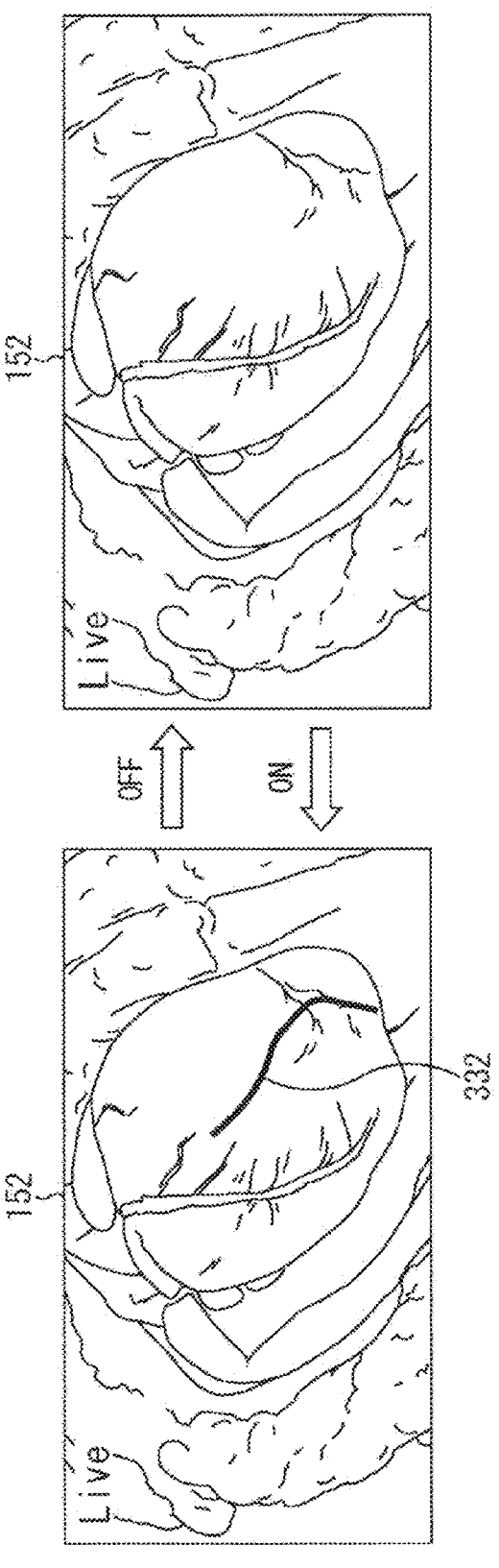
FIG. 15 illustrates a display example of an operative field image in the annotation writing processing.

Here, as illustrated in FIG. 15, in an operative field image that is displayed in the second display region 152 and that the surgeon is viewing, the display/non-display (the ON/OFF state of a superimposition display) of the annotation 332 may be switched according to an operation of the surgeon. By doing this, the display itself of the annotation 332 can be suppressed from disturbing the advance of surgery.

Furthermore, in addition to the example of FIG. 15, in an operative field image displayed in the first display region 151, the ON/OFF state of a superimposition display of the annotation 331 may be switched according to an operation of the advising doctor.

Note that an annotation that has been written to an operative field image displayed in the first display region 151 is reflected in an operative field image displayed in the second display region 152 in the description above, but a function inverse to this may be provided. In other words, an annotation that has been written to an operative field image displayed in the second display region 152 may be reflected in an operative field image displayed in the first display region 151.

By employing the configuration described above, for example, two surgeons can advance surgery while performing interactive communication such as the mutual confirmation of a position to be operated and the like.

3. Display Mode of Operative Field Image

Here, a display mode of operative field images that are displayed in the first display region 151 and the second display region 152 by the display controller 132 is described.

Figure 16:
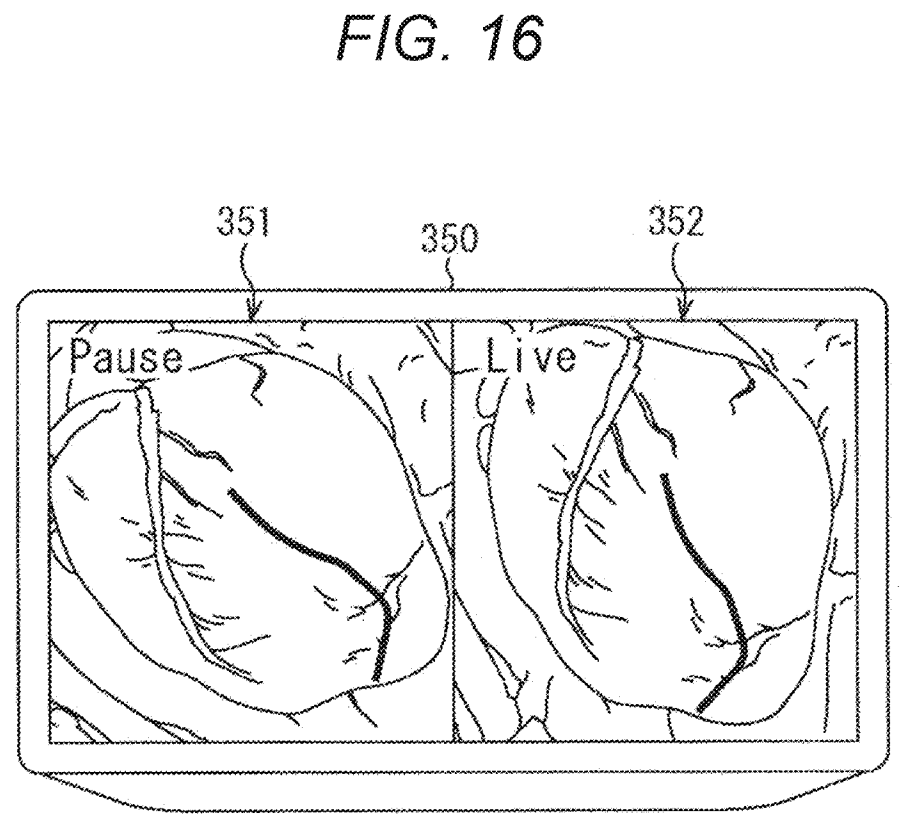

FIG. 16 illustrates a first example of a display mode of an operative field image.

In the example of FIG. 16, the first display region 351 and the second display region 352 are displayed side by side on a screen of a single display device 350.

Figure 17:
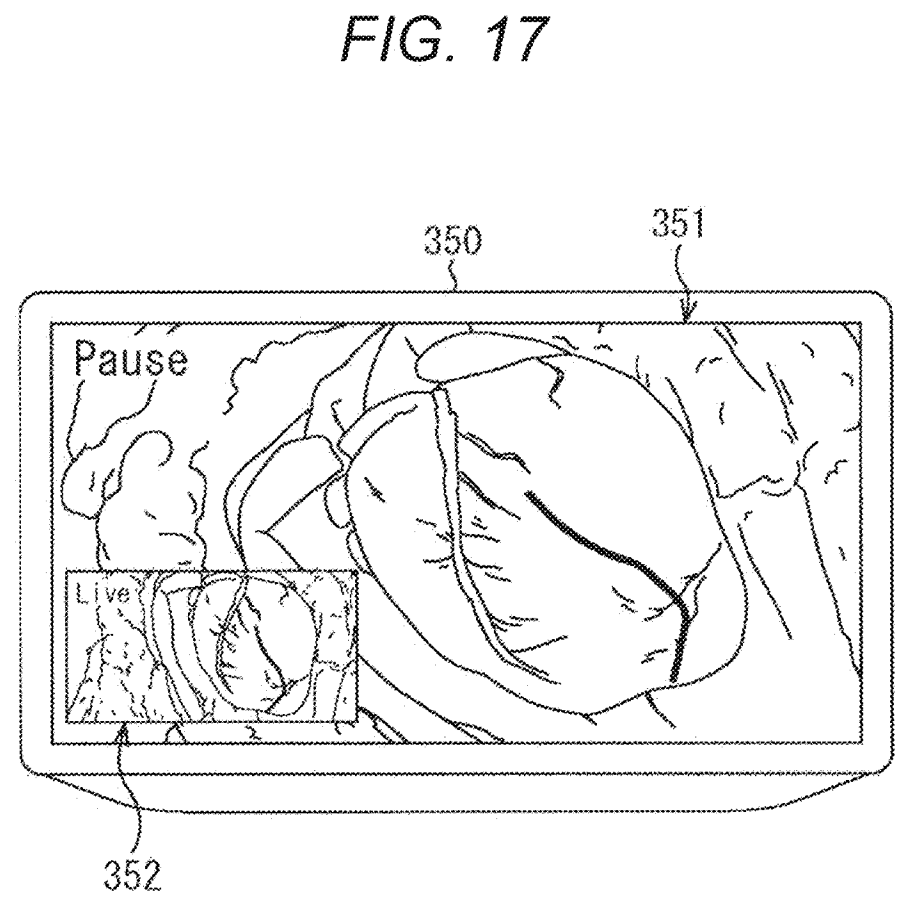

FIG. 17 illustrates a second example of a display mode of an operative field image.

In the example of FIG. 17, the first display region 351 and the second display region 352 are displayed in a picture-in-picture form on a screen of a single display device 350. Specifically, in a lower left-hand portion of the first display region 351 that is displayed on the entirety of the screen of the display device 350, the second display region 352 that is smaller than the first display region 351 is provided.

Figure 18:
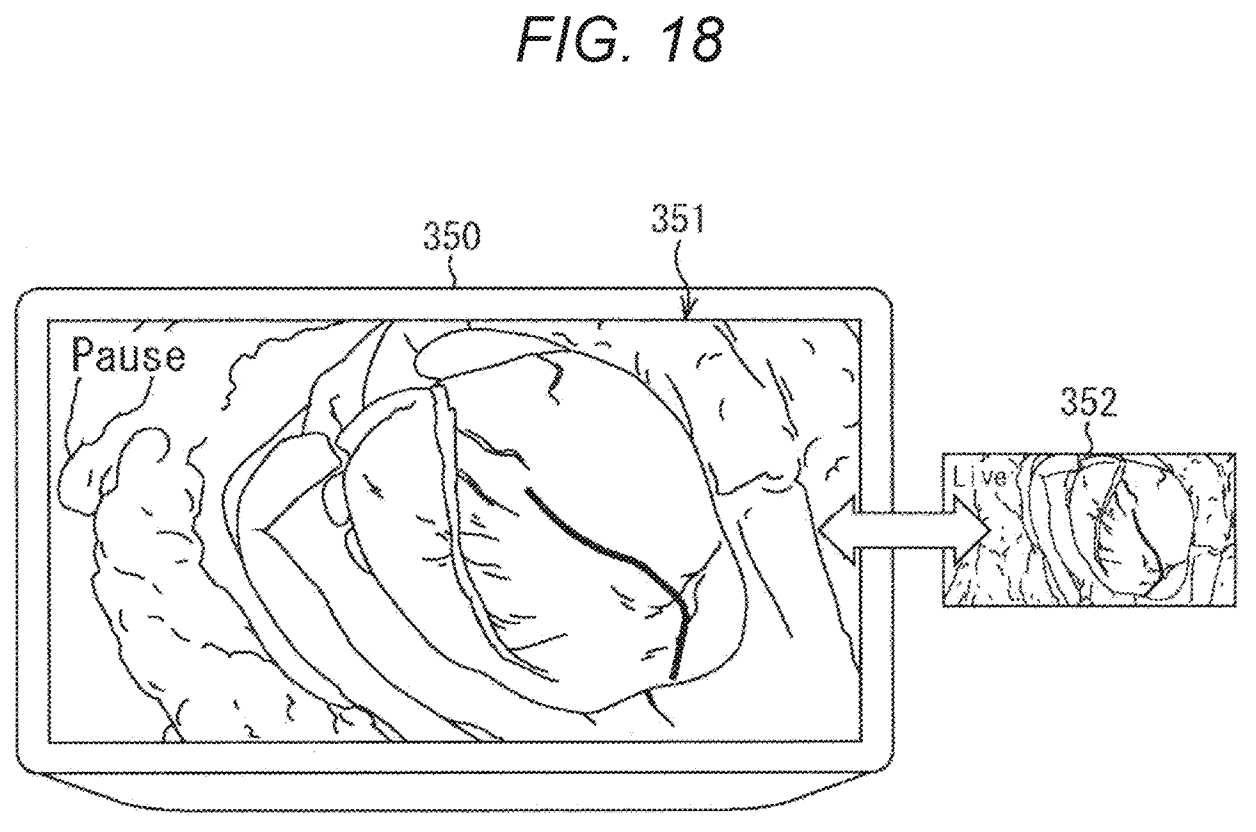

FIG. 18 illustrates a third example of a display mode of an operative field image.

The example of FIG. 18 indicates a state where the first display region 351 and the second display region 352 are switched and displayed on a screen of a single display device 350.

Figure 19:
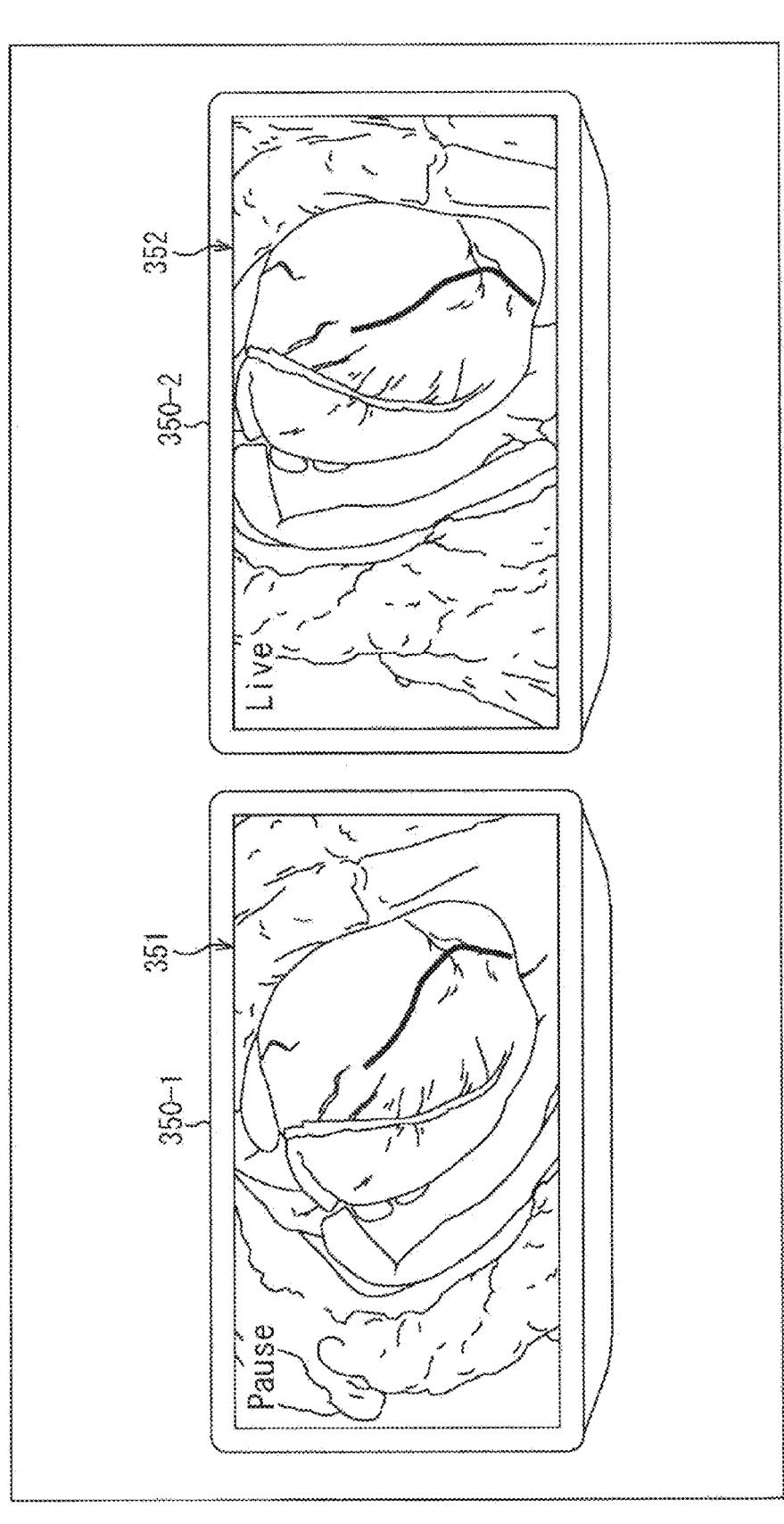
FIG. 19 is a diagram explaining a display mode of an operative field image.

FIG. 19 illustrates a fourth example of a display mode of an operative field image.

As illustrated in the example of FIG. 19, the first display region 351 and the second display region 352 may be respectively displayed in individual display devices 350-1 and 350-2 that are connected to each other via a communication line.

By employing the configuration of FIG. 19, the display devices 350-1 and 350-2 can be provided in positions that are physically separate from each other, and this enables an advising doctor to present an annotation to a surgeon who is located in a remote place.

<4. Variations>

Variations of the embodiment described above are described below.

(Writing of Annotation to Past Operative Field Image)

The writing of an annotation to a past operative field image for a prescribed time period may be accepted in addition to the writing of an annotation to an operative field image displayed in real time or a still image serving as a single prescribed frame of the operative field image.

Figure 20:
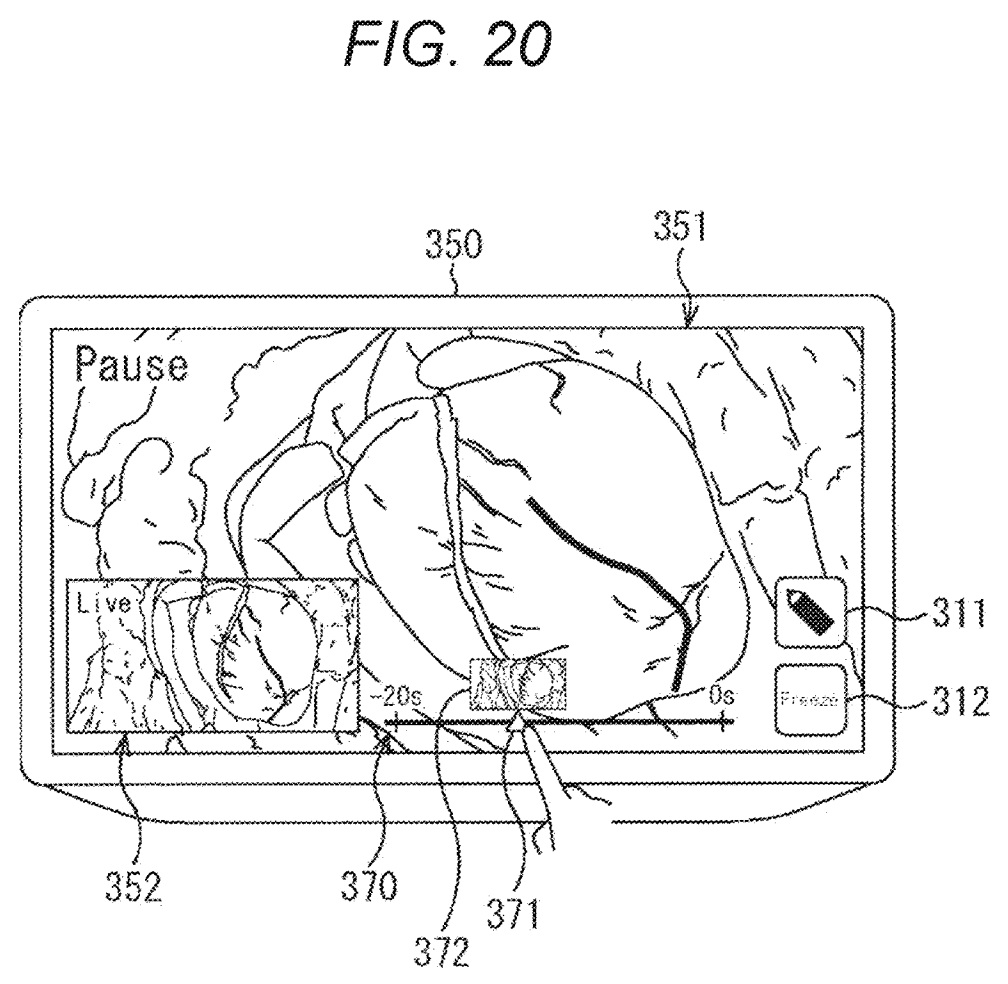

FIG. 20 illustrates an example of the writing of an annotation to a past operative field image.

In the example of FIG. 20, similarly to the example of FIG. 17, the first display region 351 and the second display region 352 are displayed in a picture-in-picture form on a screen of a single display device 350.

Moreover, in the example of FIG. 20, for example, a seek bar 370 is displayed on a right-hand side of the second display region 352, and the seek bar 370 enables a temporal position in a past operative field image for a prescribed time period, such as 20 seconds, to be specified. A right-hand end of the seek bar 370 indicates the present time, and a left-hand end of the seek bar 370 indicates 20 seconds before the present time. On the seek bar 370, a slider 371 that is used to specify a temporal position in the past operative field image and a thumbnail 372 of a frame in the specified temporal position in the operative field image are displayed.

A user operates the slider 371 on the seek bar 370 so as to specify a temporal position in the operative field image for the past 20 seconds. By doing this, a still image serving as a frame in the specified temporal position in the operative field image is displayed in the first display region 351.

Then, the user writes an annotation to the still image displayed in the first display region 351, so that the annotation can be reflected in a current operative field image that is displayed in real time in the second display region 352.

As described above, an annotation can also be written to a past operative field image.

(Masking Display)

In the description above, in a case where a position in which an annotation has been written is not located in a region in which the three-dimensional surface map data has been sufficiently constructed, the annotation is not reflected in an operative field image displayed in real time.

The present disclosure is not limited to this, and a masking display may be conducted on a region in which the three-dimensional surface map data has not been sufficiently constructed.

Figure 21:
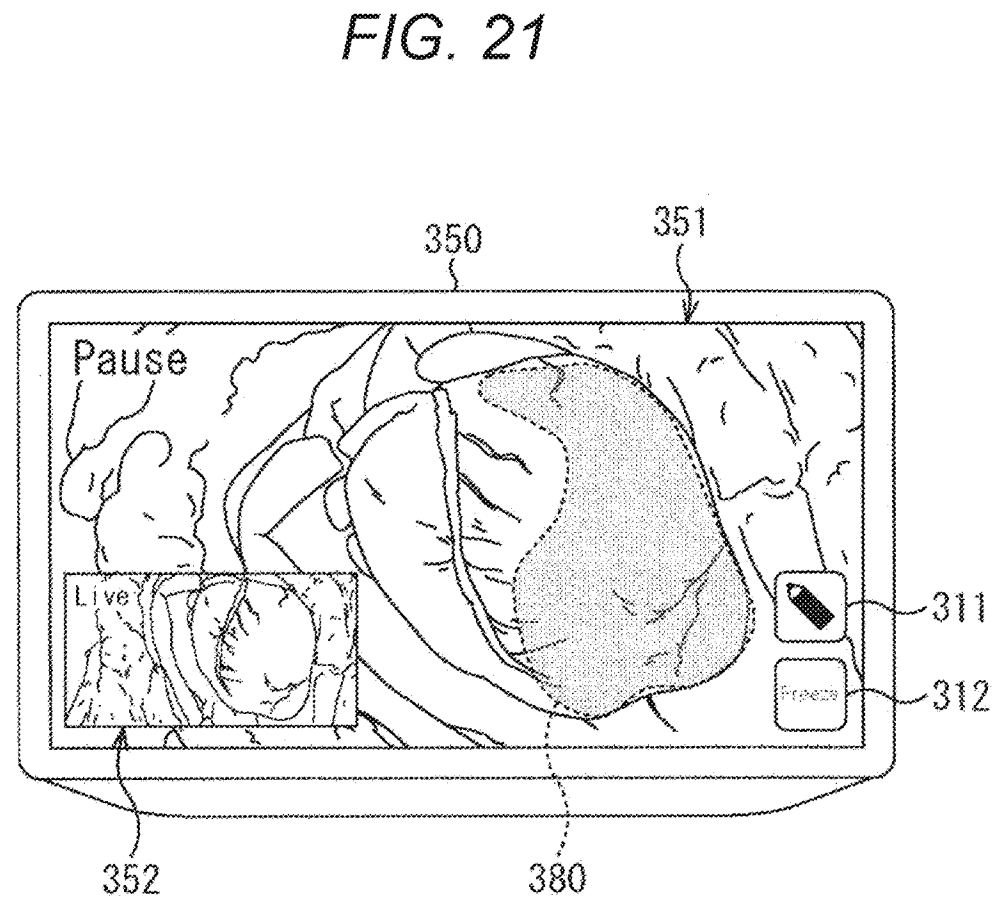

FIG. 21 illustrates an example of a masking display.

In the example of FIG. 21, similarly to the example of FIG. 17, the first display region 351 and the second display region 352 are displayed in a picture-in-picture form on a screen of the display device 350. In the example of FIG. 21, it is assumed that the freeze mode has been selected, and that a still image is displayed in the first display region 351 and a real-time operative field image is displayed in the second display region 352.

Furthermore, a masking display 380 has been conducted on a partial region of an organ that is photographed in the still image displayed in the first display region 351. The writing of an annotation is not accepted in the region on which the masking display 380 has been conducted.

By doing this, an annotation can be suppressed from being written to a region in which the three-dimensional surface map data has not been sufficiently constructed, and as a result, a reduction in the tracking accuracy of the annotation can be avoided.

(Preview Display of Three-Dimensional Image)

A preview of a three-dimensional image may be displayed so that, for example, a user can confirm whether or not an annotation written by the user has been superimposed onto an intended region.

Figure 22:
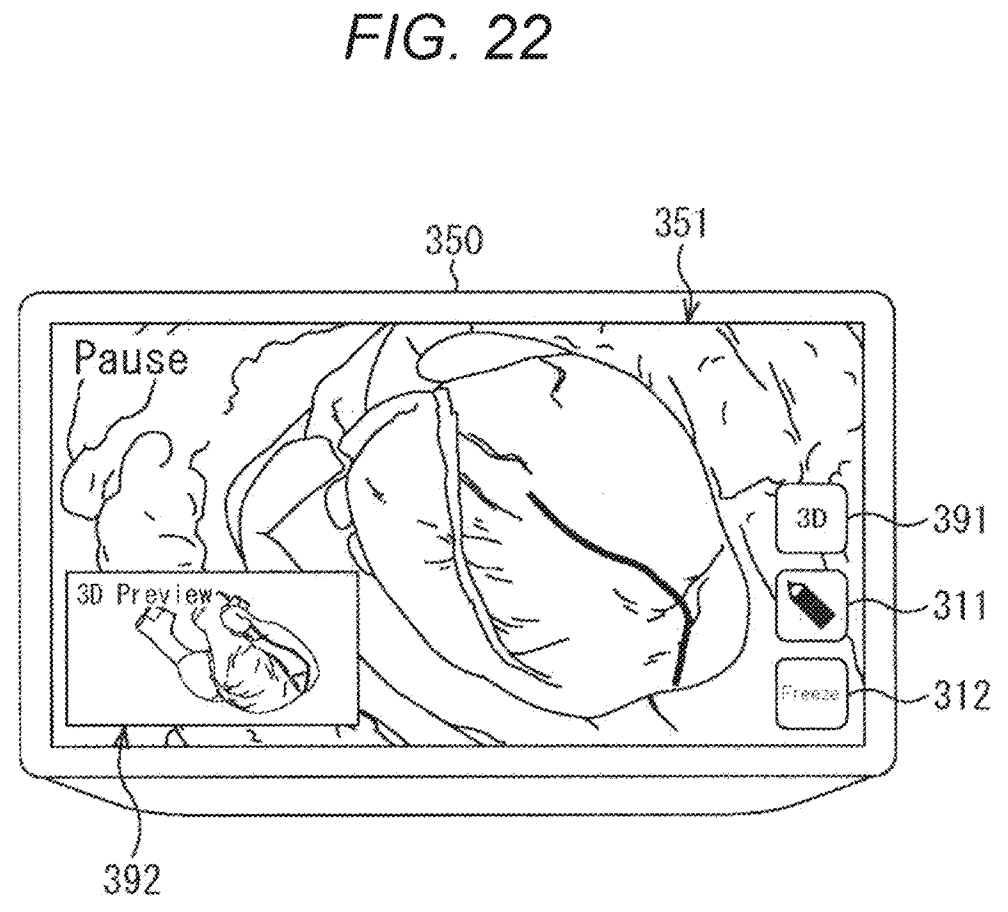

FIG. 22 illustrates an example of a preview display of a three-dimensional image.

In the example of FIG. 22, the first display region 351 is displayed on the entirety of a screen of the display device 350. In the example of FIG. 22, it is assumed that the freeze mode has been selected, and that a still image is displayed in the first display region 351.

Moreover, in the example of FIG. 22, a three-dimensional image display button 391 is displayed in addition to the writing mode button 311 and the freeze mode button 312 at a right-hand end of the screen of the display device 350.

When an annotation is written to an operative field image displayed in the first display region 351 and an operation to touch the three-dimensional image display button 391 is performed, a three-dimensional image 392 based on the three-dimensional information (the three-dimensional surface map data) is displayed in a lower left-hand portion of the first display region 351.

In the three-dimensional image 392, an orientation and an angle in/at which a subject is displayed can be freely changed according to a user's operation. In the example of FIG. 22, in the three-dimensional image 392, an annotation has been superimposed onto a position that corresponds to the specified position (a position in which the annotation has been written) of the still image displayed in the first display region 351.

As described above, the three-dimensional image 392 in which an annotation has been superimposed is displayed, so that a user can easily confirm whether or not an annotation that the user themselves has written has been superimposed onto an intended position.

(Method for Writing Annotation)

In the description above, the writing of an annotation (the specification of the specified position) is implemented by performing an operation to touch a display device having a touch panel function, but the writing of the annotation may be implemented by using another method.

For example, a coordinate position in which an annotation will be written on a screen may be input by using a mouse, or the coordinate position may be obtained by performing image recognition on a region that is specified by an operation tool, such as forceps, that is photographed on the screen.

Moreover, an instruction to write an annotation may be issued by using sound, or the instruction to write the annotation may be issued by using a line of sight or the orientation of a body of a user.

Furthermore, the instruction to write the annotation is not only issued by using a method for directly specifying the coordinate position on the screen.

Figure 23:
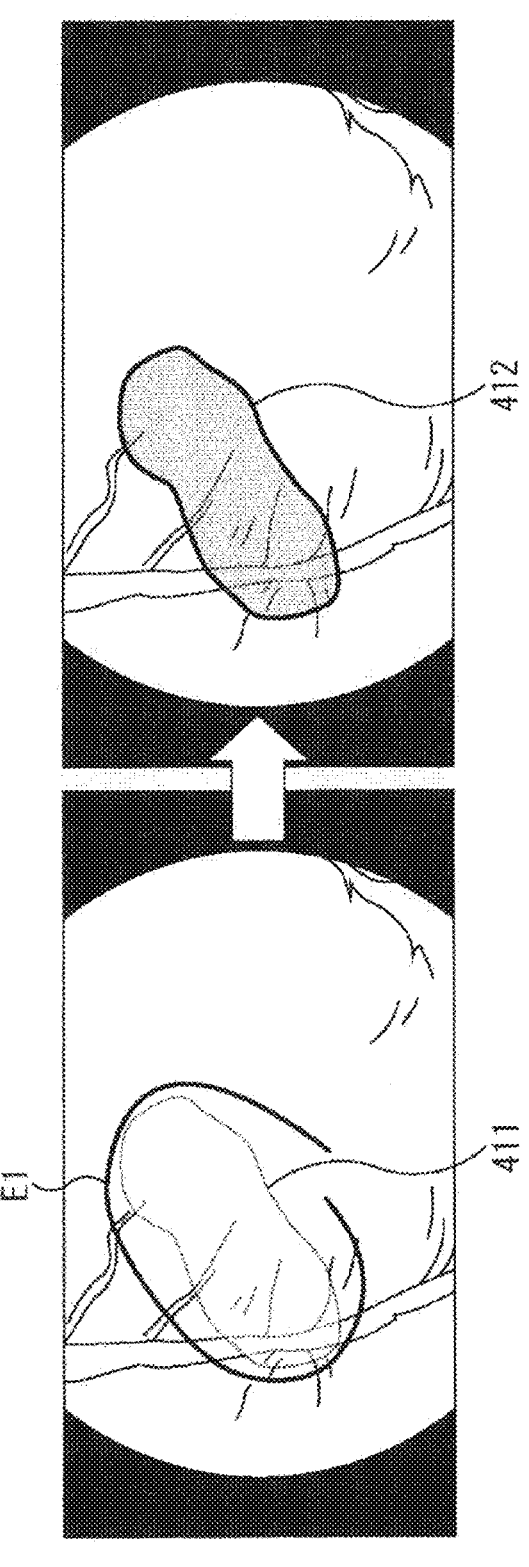
FIG. 23 is a diagram explaining a method for writing an annotation.

For example, in a case where an instruction to write an annotation specifying a region is issued, the boundary of a cancer region 411 to be specified is automatically recognized by surrounding the cancer region 411 with a frame E1, as illustrated in a left-hand portion of FIG. 23. Then, an annotation 412 indicating the cancer region 411 is displayed, as illustrated in a right-hand portion of FIG. 23.

Furthermore, an annotation may be suppressed from being written by segmenting the three-dimensional surface map data into organs and masking the surface of each of the organs.

In the surgery assistance system according to this embodiment, examples of an organ to which an annotation is written include individual internal organs, a blood vessel, a tumor, the lymphatic system, the nerve, adipose tissue, the abdominal wall, a bleeding region, a discolored region, and the like. Accordingly, the writing of an annotation can also be utilized, for example, to display a holding position or a punctured part of each of the organs described above.

Display Example of Annotation

An annotation may be a point image indicating a point (a specified position) specified by a user on a screen or a line image indicating a line serving as a set of points. Examples of the line described above include a line segment connecting two points, a polygonal line configured by a plurality of line segments, a curve drawn by a user, a closed polygonal line, and a closed curve. Furthermore, the annotation may be a plane image indicating a region surrounded with a closed polygonal line or a closed curve. Examples of the plane image include a geometric pattern that indicates a region having volume in addition to a surface region of an organ.

As described above, the annotation can employ a display form according to usage.

Moreover, by using the three-dimensional surface map data (the three-dimensional information), an annotation indicating a position and a region of the surface of an organ photographed in an operative field image and a position and a region in a depth direction (a stereoscopic region) of the organ may be written (superimposed). The three-dimensional information is associated with each of these positions and regions, and therefore a distance between points or the area/volume of a region can be virtually calculated without directly touching the organ.

Figure 24:
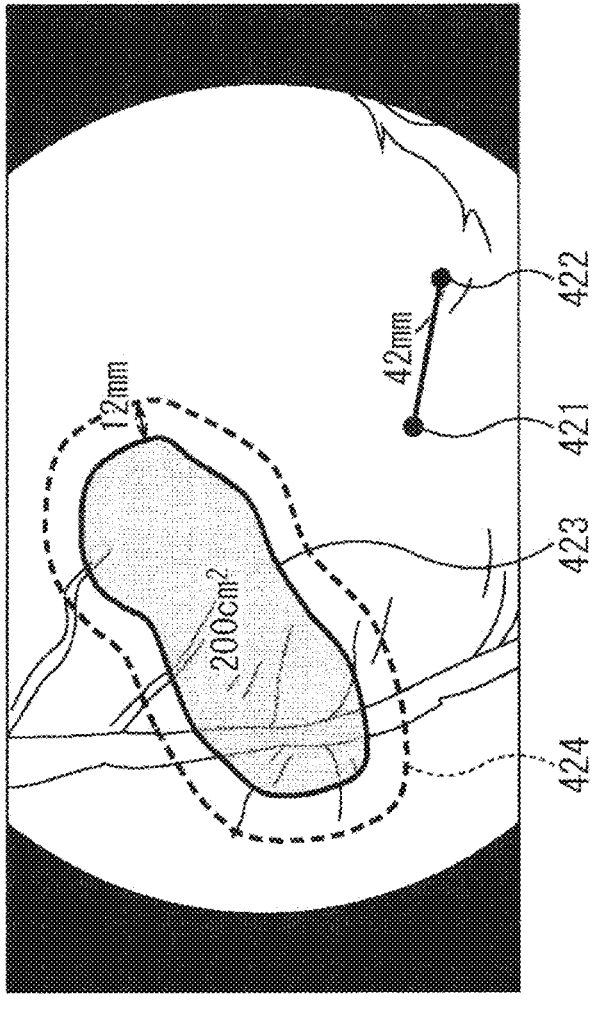
FIG. 24 illustrates a display example of an annotation.

For example, in the example of FIG. 24, a line image connecting point images 421 and 422 and a plane image 423 of the surface of an organ photographed in an operative field image are superimposed as an annotation onto the operative field image. In the example of FIG. 24, a distance between the point image 421 and the point image 422 is calculated to be 42 mm, and the area of the plane image 423 is calculated to be 200 mm$^2$.

Note that a closed curve 424 that surrounds the plane image 423 so as to be spaced apart from the boundary of the plane image 423 by a prescribed distance (for example, 12 mm) may be superimposed as an annotation onto the operative field image, as illustrated in FIG. 24.

Figure 25:
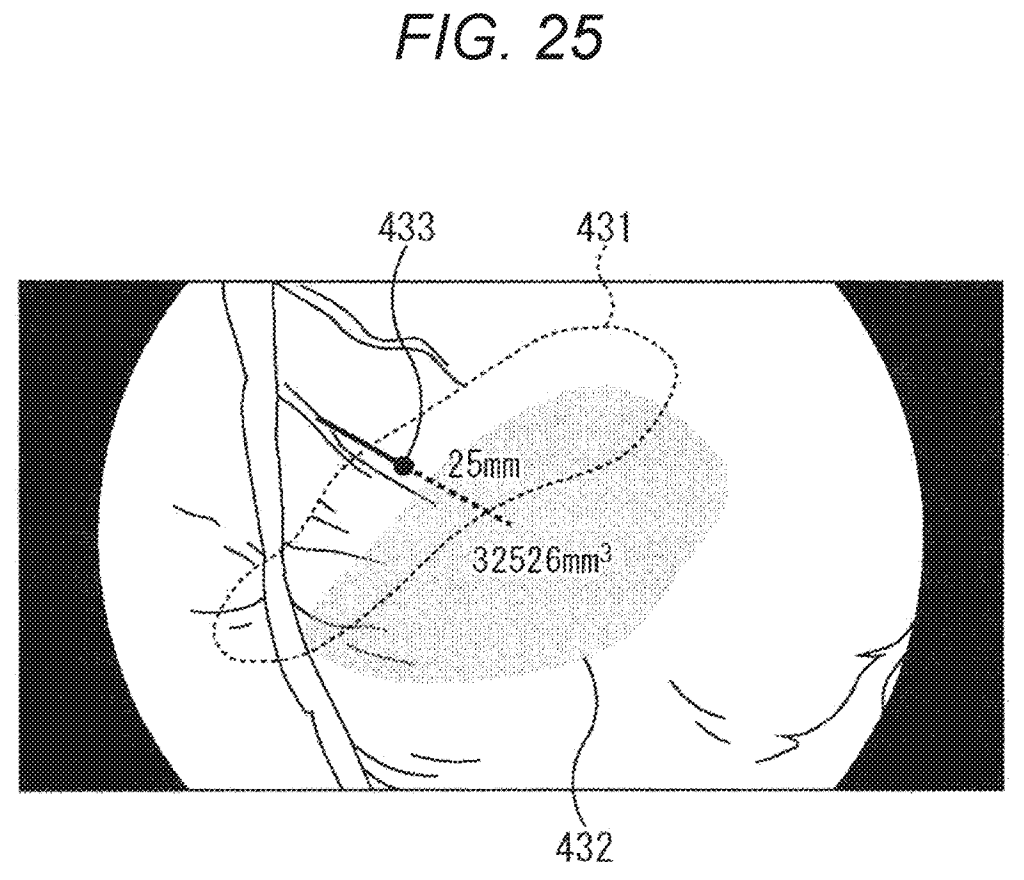

Furthermore, in the example of FIG. 25, a stereoscopic image 432 having volume in a depth direction of a region 431 of the surface of an organ photographed in an operative field image, and a point image 433 on the region 431 are superimposed as an annotation onto the operative field image. In the example of FIG. 25, the volume of the stereoscopic image 432 is calculated to be 32526 mm$^3$, and a distance between the point image 433 and the stereoscopic image 432 is calculated to be 25 mm.

Moreover, perspective may be given to a point image or a plane image that is displayed as an annotation by changing the color or density of the point image or the plane image according to a distance from an observation optical system of the endoscope 11 so that a user can intuitively grasp a three-dimensional position of the annotation.

Furthermore, an example has been described above in which a single user (for example, an advising doctor) writes an annotation to an operative field image displayed in a single display region (the first display region 151). The present disclosure is not limited to this, and a plurality of advising doctors may write annotations to an operative field image displayed in a single display region. Furthermore, a display region may be provided for each of a plurality of advising doctors, and each of the plurality of advising doctors may write an annotation to an operative field image displayed in each of the plurality of display regions.

Figure 26:
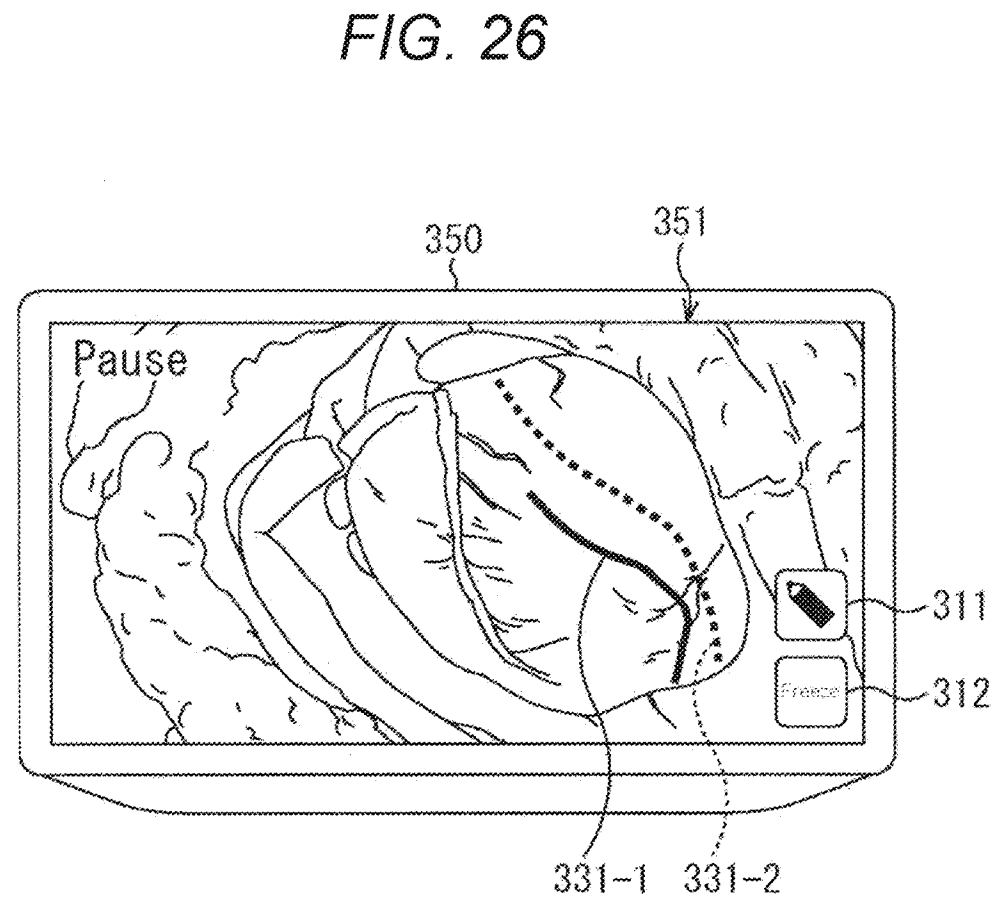

In this case, annotations having display forms different from each other may be superimposed, for example, by changing color or shape according to each of the plurality of advising doctors who have written the annotations (each user who has specified the specified position on the operative field image). For example, as illustrated in FIG. 26, an annotation 331-1 that has been written by a first advising doctor is displayed with a solid line, and an annotation 331-2 that has been written by a second advising doctor is displayed with a dotted line.

By doing this, it can be discriminated who has written an annotation that has been superimposed onto an operative field image.

Furthermore, in the example described above, from among annotations written by a plurality of users, an annotation written by a specific user may be reset (deleted).

Moreover, an image or three-dimensional information that has been obtained by another modality (a device that photographs a medical image, such as a computed tomography (CT) device or a magnetic resonance imaging (MRI) device) may be superimposed onto an operative field image. By doing this, an annotation can be displayed as if the annotation were written inside an organ.

In addition, by displaying various types of information relating to a region in a position that is a start point of the writing of an annotation, useful information can be presented to a user themselves or another user or attention of the user themselves or the other user can be called, when the user themselves or the other user confirms the region at a later time.

(Writing of Annotation to Recorded Operative Field Image)

In the description above, an annotation is written to an operative field image that is captured by the sensing unit 110 and is displayed in real time. The present disclosure is not limited t to this, and an operative field image captured by the sensing unit 110 may be recorded, and an annotation may be written to the recorded operative field image. The form described above can be utilized in a medical education site and the like.

(Obtainment of Absolute Three-Dimensional Information)

In this embodiment, relative three-dimensional information is obtained on the basis of a camera position/posture obtained in movement estimation. However, absolute three-dimensional information using, as a reference, the outside of a body cavity of a patient to be observed may be obtained. Specifically, an optical and magnetic tracking system that has an image recognition function and that includes a reference coordinate system outside the body cavity of the patient is provided in the endoscope 11, and absolute three-dimensional information is obtained by using the coordinate system as a reference. This enables an absolute three-dimensional position of an annotation to be presented.

(Utilization of Machine Learning)

In recent years, tumors and the like have been able to be automatically detected by using AI such as machine learning or deep learning, and a result of the detection above may be used as an annotation. By doing this, an annotation can continue to be superimposed and displayed in the position or region of a tumor that has been detected in a certain frame of an operative field image. Also in this case, by enabling the ON/OFF state of the superimposition display of the annotation to be switched, the display itself of the annotation can be suppressed from hindering the progress of surgery.

<5. Application>

Figure 27:
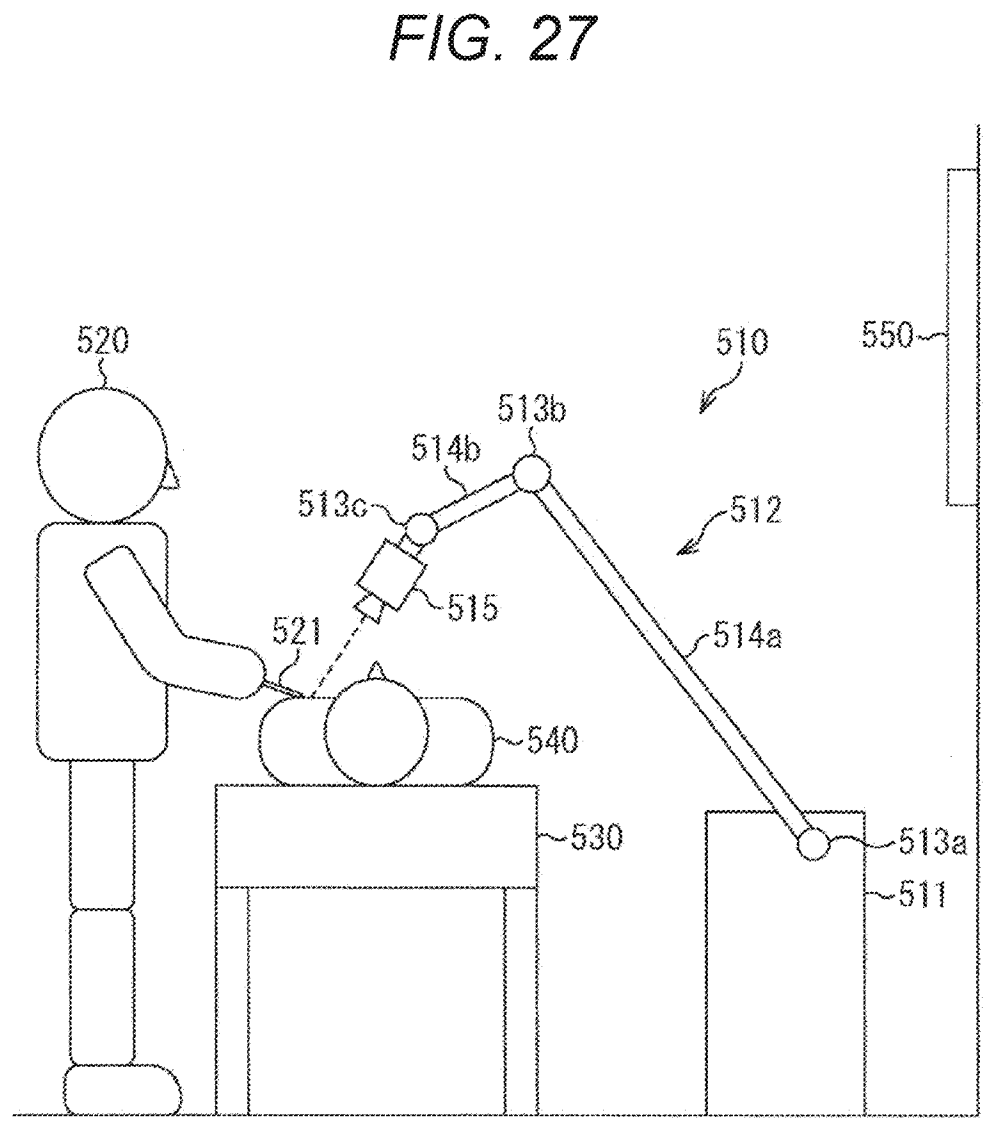

Next, an example of a case where a video microscope apparatus for surgery that includes an arm is used is described as another application of the surgery assistance system according to this embodiment with reference to FIG. 27.

FIG. 27 illustrates an example of a microscope surgery system using a video microscope apparatus for surgery that serves as medical equipment for observation that observes the inside of a patient's body.

FIG. 27 illustrates a state in which a doctor serving as an operator (a user) 520 is performing surgery on an object to be operated (a patient) 540 on an operating table 530 by using a tool for surgery 521 such as a scalpel, tweezers, or forceps.

Note that, in the description below, it is assumed that an operation is a general term for various types of medical treatment such as surgery and inspection that are performed on a patient serving as the object to be operated 540 by a doctor serving as the user 520. Furthermore, the example of FIG. 27 indicates a state of surgery as an example of the operation. However, an operation in which a video microscope apparatus for surgery 510 is used is not limited to surgery, and may be various other operations.

On the side of the operating table 530, the video microscope apparatus for surgery 510 according to this embodiment is provided.

The video microscope apparatus for surgery 510 includes a base unit 511 serving as a base, an arm unit 512 that extends from the base unit 511, and an imaging unit 515 that is connected as an end unit to the end of the arm unit 512.

The arm unit 512 includes a plurality of joint units 513*a*, 513*b*, and 513*c*, a plurality of links 514*a* and 514*b* that are coupled by the joint units 513*a* and 513*b*, and the imaging unit 515 that is provided at the end of the arm unit 512.

In the example of FIG. 27, the arm unit 512 includes three joint units 513*a* to 513*c* and two links 514*a* and 514*b* for simplification. In practice, considering a degree of freedom of the positions and postures of the arm unit 512 and the imaging unit 515, the numbers and shapes of the joint units 513*a* to 513*c* and the links 514*a* and 514*b*, the directions of driving shafts of the joint units 513*a* to 513*c*, and the like may be appropriately set in such a way that a desired degree of freedom is achieved.

The joint units 513*a* to 513*c* have a function of rotatably coupling the links 514*a* and 514*b* to each other, and the rotation of the joint units 513*a* to 513*c* is driven, so that the driving of the arm unit 512 is controlled.

The imaging unit 515 is connected as an end unit to the end of the arm unit 512.

The imaging unit 515 is a unit that captures an image of an object to be imaged by including an optical system that captures an optical image of a subject, and the imaging unit 515 is configured, for example, as a camera that is capable of capturing a moving image and a still image, or the like. As illustrated in FIG. 27, the postures and positions of the arm unit 512 and the imaging unit 515 are controlled by the video microscope apparatus for surgery 510 in such a way that the imaging unit 515 provided at the end of the arm unit 512 images a state of a region to be operated of the object to be operated 540.

Note that the configuration of the imaging unit 515 that is connected as an end unit to the end of the arm unit 512 is not particularly limited, and the imaging unit 515 may be configured, for example, as an endoscope or a microscope.

Furthermore, the imaging unit 515 may be configured so as to be attachable to or detachable from the arm unit 512.

By employing the configuration described above, for example, an imaging unit 515 according to usage may be appropriately connected as an end unit to the end of the arm unit 512. Note that description is made here focusing on a case where the imaging unit 515 is employed as an end unit, but it goes without saying that an end unit that is connected to the end of the arm unit 512 is not limited to the imaging unit 515.

Furthermore, a display device 550, such as a monitor or a display, is provided in a position facing the user 520. For example, an image processing device that is incorporated into or externally attached to the video microscope apparatus for surgery 510 performs various types of image processing on an image of the region to be operated that has been captured by the imaging unit 515, and the image is displayed as an electronic image on a display screen of the display device 550.

By employing the configuration described above, the user 520 can perform various types of treatment (such as surgery) while viewing the electronic image of the region to be operated that is displayed on the display screen of the display device 550.

Here, in the example of FIG. 27, the imaging unit 515 includes, for example, the sensing unit 110 described with reference to FIG. 3. Furthermore, the image processing device that performs various types of image processing on the image of the region to be operated that has been captured by the imaging unit 515 corresponds to an example of the information processing device 130 described with reference to FIG. 3. Similarly, the display device 550 corresponds to an example of the display device 150 described with reference to FIG. 3.

<6. Hardware Configuration>

Next, an example of the hardware configuration of an information processing device that configures the surgery assistance system according to this embodiment is described in detail with reference to FIG. 28.

Figure 28:
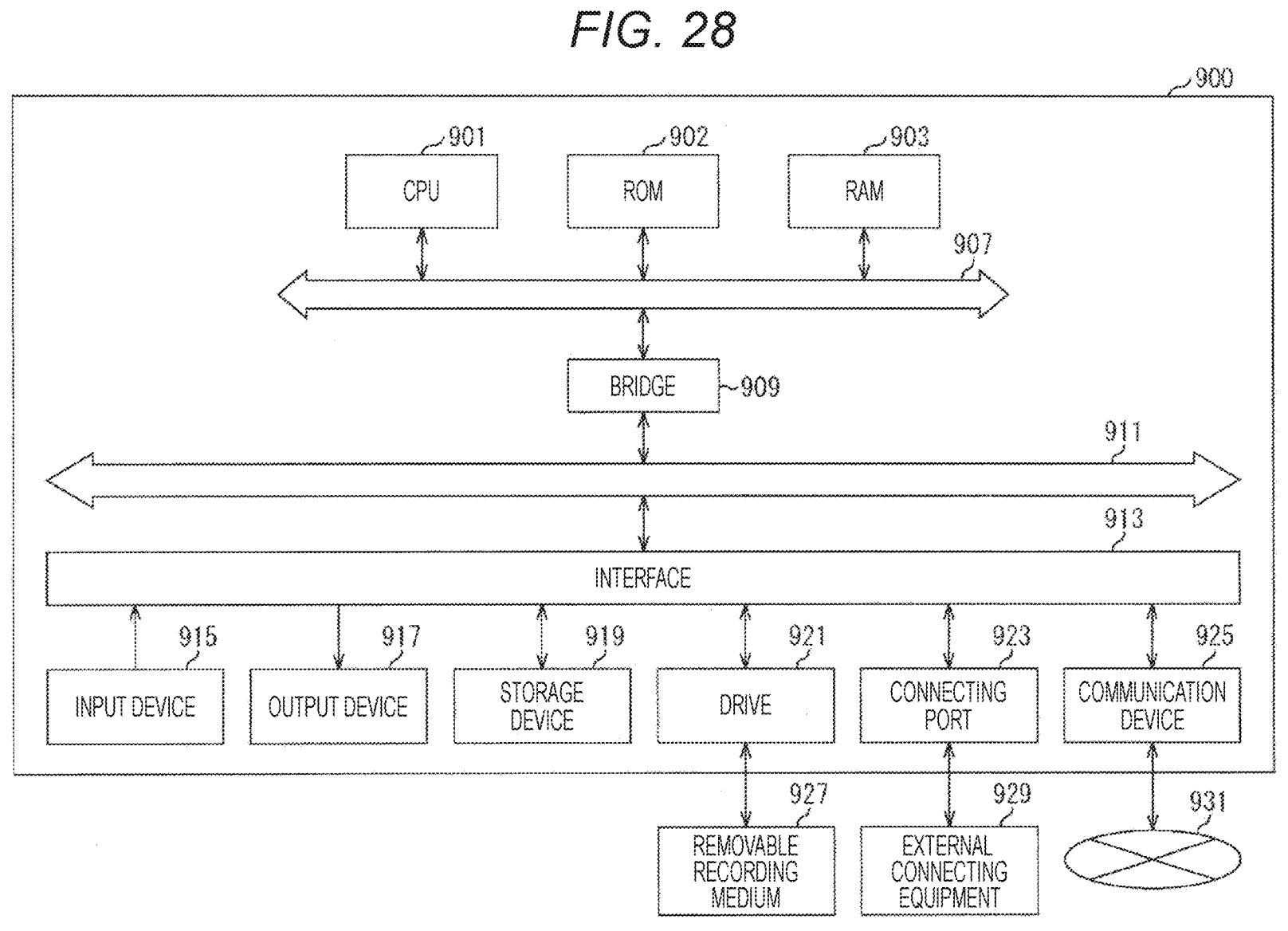

FIG. 28 is a block diagram illustrating an example of the hardware configuration of an information processing device 900 that configures the surgery assistance system according to this embodiment.

As illustrated in FIG. 28, the information processing device 900 includes a CPU 901, a ROM 903, and a RAM 905. Moreover, the information processing device 900 includes a host bus 907, a bridge 909, an external bus 911, an interface 913, an input device 915, an output device 917, and a storage device 919. Note that the information processing device 900 may include a drive 921, a connecting port 923, and a communication device 925.

The CPU 901 functions as an arithmetic processing device and a controller, and controls the entirety or part of an operation in the information processing device 900 in accordance with various programs recorded in the ROM 903, the RAM 905, the storage device 919, or a removable recording medium 927.

The ROM 903 stores a program, an operation parameter, and the like that are used by the CPU 901. The RAM 905 transitorily stores a program to be used by the CPU 901, a parameter that appropriately changes in the execution of the program, and the like. The ROM 903 and the RAM 905 are connected to each other via the host bus 907 that is configured by an internal bus such as a CPU bus. Note that respective configurations of the information processing device 130 that have been described with reference to FIG. 3 are implemented, for example, by the CPU 901.

The host bus 907 is connected to the external bus 911, such as a peripheral component interconnect/interface (PCI) bus, via the bridge 909. The input device 915, the output device 917, the storage device 919, the drive 921, the connecting port 923, and the communication device 925 are connected to the external bus 911 via the interface 913.

The input device 915 is an operation unit that is operated by a user, such as a mouse, a keyboard, a touch panel, a button, a switch, a lever, or a pedal. Furthermore, the input device 915 may be, for example, a remote control unit (what is called a remote controller) that uses infrared rays or other radio waves, or may be external connecting equipment 929, such as a mobile phone or a PDA, that corresponds to an operation performed on the information processing device 900.

The input device 915 is configured, for example, by an input control circuit or the like that generates an input signal on the basis of information that a user has input using the operation unit described above and that outputs the input signal to the CPU 901.

The user operates the input device 915 so as to be able to input various types of data to the information processing device 900 or to issue an instruction to perform a processing operation to the information processing device 900.

The output device 917 is configured by a device that is capable of visually or aurally reporting the obtained information to the user. Specifically, the output device 917 is configured as a CRT display device, a liquid crystal display device, a plasma display device, an EL display device, a display device such as a lamp, a sound output device such as a speaker or a headphone, a printer device, or the like.

The output device 917 outputs, for example, results obtained by the information processing device 900 performing various types of processing. Specifically, the display device displays the results obtained by the information processing device 900 performing the various types of processing in the form of text or an image. On the other hand, the sound output device converts an audio signal configured by reproduced sound data, acoustic data, or the like into an analog signal, and outputs the analog signal. Note that the display device 150 described with reference to FIG. 3 is implemented, for example, by the output device 917.

The storage device 919 is a device for data storage that is configured as an example of a storage of the information processing device 900. The storage device 919 is configured, for example, by a magnetic storage device such as a hard disk drive (HDD), a semiconductor storage device, an optical storage device, a magneto-optical storage device, or the like. The storage device 919 stores a program to be executed by the CPU 901, various types of data, or the like.

The drive 921 is a reader/writer for a recording medium, and is incorporated into or externally attached to the information processing device 900. The drive 921 reads information recorded in the attached removable recording medium 927 such as a magnetic disk, an optical disk, a magneto-optical disk, or a semiconductor memory, and outputs the information to the RAM 905. Furthermore, the drive 921 can write a record to the attached removable recording medium 927 such as a magnetic disk, an optical disk, a magneto-optical disk, or a semiconductor memory.

The removable recording medium 927 is, for example, a DVD medium, an HD-DVD medium, a Blu-ray (registered trademark) medium, or the like. Furthermore, the removable recording medium 927 may be a CompactFlash (registered trademark) (CF), a flash memory, a secure digital (SD) memory card, or the like. Moreover, the removable recording medium 927 may be, for example, an integrated circuit (IC) card mounting a non-contact IC chip, electronic equipment, or the like.

The connecting port 923 is a port that directly connects the external connecting equipment 929 to the information processing device 900. Examples of the connecting port 923 include a universal serial bus (USB) port, an IEEE 1394 port, a small computer system interface (SCSI) port, and the like. Other examples of the connecting port 923 include an RS-232C port, an optical audio terminal, a high-definition multimedia interface (HDMI) (registered trademark) port, and the like. By connecting the external connecting equipment 929 to the connecting port 923, the information processing device 900 directly obtains various types of data from the external connecting equipment 929, or provides various types of data to the external connecting equipment 929.

The communication device 925 is, for example, a communication interface that is configured by a communication device for connection with a communication network (a network) 931, and the like. The communication device 925 is, for example, a wired or wireless local area network (LAN), Bluetooth (registered trademark), a communication card for a wireless USB (WUSB), or the like. Furthermore, the communication device 925 may be a router for optical communication, a router for asymmetric digital subscriber line (ADSL), a modem for various types of communication, or the like.

For example, the communication device 925 can transmit or receive a signal to/from, for example, the Internet or other communication equipment according to a prescribed protocol such as TCP/IP. Furthermore, the communication network 931 connected to the communication device 925 may be configured by a network that is connected by wire or wirelessly, and the like. The communication network 931 may be, for example, the Internet or an in-house LAN, or may be a communication network in which infrared communication, radio wave communication, or satellite communication is performed.

Each of the components described above of the information processing device 900 may be configured using a general-purpose member, or may be configured by hardware specialized for a function of each of the components. Accordingly, a hardware configuration to be used can be appropriately changed according to a technique level at the time of the implementation of this embodiment.

Moreover, a computer program for implementing each of the functions of the information processing device 900 that configures the surgery assistance system according to this embodiment can be generated, and the computer program can be mounted onto a personal computer or the like. Furthermore, a computer-readable recording medium that stores the computer program described above can also be provided. The recording medium is, for example, a magnetic disk, an optical disk, a magneto-optical disk, a flash memory, or the like. Furthermore, the computer program may be distributed, for example, via the network without using the recording medium.

<7. Summary>

As described above, in a surgery assistance system according to an embodiment of the present disclosure, an annotation is superimposed onto a specified position that has been specified by a user on an operative field image displayed in a first display region. Then, the annotation is superimposed while tracking the specified position on an operative field image that is displayed in real time in a second display region.

By doing this, the writing of an annotation to an operative field image displayed in the first display region that has been performed by an advising doctor is reflected in an operative field image that is displayed in the second display region and that a surgeon is viewing.

In the related art, endoscopic surgery or surgery using a microscope is surgery via a screen, and therefore it is difficult to orally communicate detailed instructions relating to a technique between operators.

In view of this, by employing a surgery assistance system according to another embodiment of the present disclosure, virtual marking using an annotation enables an advising doctor in a leadership position, a surgeon, an assistant, and a paramedic to cooperate with each other.

Furthermore, by employing a surgery assistance system according to yet another embodiment of the present disclosure, marks can be put on an operative field image for educational purposes, or marks can be put on a recorded operative field image at a later time.

In the virtual marking described above, invasive marks are not directly put on organs, or instructions are not issued using forceps and the like, and therefore organs are not damaged. Furthermore, when a plan for surgery is built, policy can be determined while putting marks, or in a case where the marks are unnecessary, new marks can be put.

Note that embodiments of the present disclosure are not limited to the embodiment described above, and various modifications can be made without departing from the scope of the present disclosure.

For example, the present disclosure can employ a configuration of cloud computing in which a plurality of devices perform processing in cooperation with each other by sharing a single function via a network.

Furthermore, the processes of the respective steps described above with reference to the flowcharts can be performed by a single device, or can be shared and performed by a plurality of devices.

Moreover, in a case where a single step includes a plurality of processes, the plurality of processes included in the single step can be performed by a single device, or can be shared and performed by a plurality of devices.

Furthermore, the present disclosure can employ the configuration described below.

(1)

A surgical assistance apparatus including:

circuitry configured to generate a first image to be displayed in a first display region and including a first operative field image of a surgical subject and a first visual annotation image superimposed on a predetermined region in an operative field of the first operative field image that corresponds to a physical region of the surgical subject, and generate a second image to be displayed in a second display region and including a second operative field image and a second visual annotation image superimposed on an estimated region of the second operative field image that corresponds to the physical region of the surgical subject.

(2)

The surgical assistance apparatus according to (1), wherein the circuitry is further configured to:

generate three-dimensional information indicating a three-dimensional structure of the surgical subject;

estimate a position of an imager that captures the second operative field image of the surgical subject; and generate the second image by superimposing the second visual annotation image on a portion of the three-dimensional structure of the surgical subject that corresponds to the estimated region and that is estimated to correspond to the physical region of the surgical subject based on the estimated movement of the imager and the generated three-dimensional information.

(3)

The surgical assistance apparatus according to (2), wherein:

the generated three-dimensional information of the surgical subject includes time information indicating a generation/update time of the corresponding three-dimensional information.

(4)

The surgical assistance apparatus according to (1), wherein:

the first visual annotation image is input by an input device configured to be used by a first user to input the first visual annotation image on the first display region without obscuring a view of the second display region by a second user.

(5)

The surgical assistance apparatus according to (4), wherein:

the input device to input the first visual annotation image is configured to be used by the first user to identify the physical region of the surgical subject as a target for a surgical action to be performed on the surgical subject; and the second visual annotation image in the second display region is configured to be used by the second user to control execution of the surgical action on the physical region of the surgical subject.

(6)

The surgical assistance apparatus according to (1), wherein:

the first display region is displayed on a first display device; and the second display region is displayed on a second display device.

(7)

The surgical assistance apparatus according to (1), wherein:

the first display region is displayed in a first window area of a display; and the second display region is displayed in a second window area of the display.

(8)

The surgical assistance apparatus according to (2), wherein:

the imager is included in an endoscope that captures the second operative field image as a moving image of an inside of the surgical subject.

(9)

The surgical assistance apparatus according to (8), wherein the circuitry is further configured to:

according to a freeze mode input from a user interface device, generate the first image as a still image obtained from the moving image of an inside of the surgical subject; and according to a writing mode input from the user interface device, receive information associating the first visual annotation image with the physical region of the surgical subject.

(10)

The surgical assistance apparatus according to (2), wherein the circuitry is further configured to update the second image to maintain the correspondence between the second visual annotation superimposed on the estimated region of the second operative field image and the physical region of the subject during a movement of the imager or a movement of the physical region of the surgical subject.

(11)

The surgical assistance apparatus according to (1), wherein the circuitry includes a programmable processor.

(12)

The surgical assistance apparatus according to (1), wherein the second operative field image includes a moving image of the surgical subject that indicates a movement of the surgical subject in real-time.

(13)

The surgical assistance apparatus according to (12), wherein the circuitry is further configured to obtain the first operative field image from the moving image of the surgical subject.

(14)

The surgical assistance apparatus according to (1), wherein the circuitry is further configured to receive information regarding the first visual annotation image from an input device operated using the first display region.

(15)

The surgical assistance apparatus according to (1), wherein the second operative field image is a moving image that indicates a movement of at least the surgical subject and the second visual annotation image moves with the movement of at least the surgical subject to maintain the correspondence between of the estimated region of the second operative field image and the physical region of the surgical subject.

(16)

The surgical assistance apparatus according to (2), wherein the circuitry is further configured to:

generate the second visual annotation image including an indication of a position in a depth direction of the second operative field image on the basis of the generated three-dimensional information.

(17)

The surgical assistance apparatus according to (2), wherein the circuitry is further configured to:

conduct a masking display on a region of the first image in which the generated three-dimensional information has not been sufficiently constructed.

(18)

The surgical assistance apparatus according to (17), wherein the circuitry is further configured to:

in a case where the estimated region of the second operation field image that corresponds to the physical region of the surgical subject includes the region of the first image in which the generated three-dimensional information has not been sufficiently constructed, the second image is generated without superimposing at least a portion of the second visual annotation image.

(19)

The surgical assistance apparatus according to (18), wherein the circuitry is further configured to:

in a case where the estimated region of the second operation field image that corresponds to the physical region of the surgical subject includes the region of the first image in which the generated three-dimensional information has not been sufficiently constructed, the first image is displayed as a still image instead of a moving image.

(20)

A surgical method including:

generating a first image to be displayed in a first display region and including a first operative field image of a surgical subject and a first visual annotation superimposed on a predetermined region of the first operative field image that corresponds to a physical region of the surgical subject; and generating a second image to be displayed in a second display region and including a second operative field image and a second visual annotation image superimposed on an estimated region of the second operative field image that corresponds to the physical region of the surgical subject.

(21)

A non-transitory computer readable medium storing instructions, which when executed by a computer cause the computer to perform steps including:

generating a first image to be displayed in a first display region and including a first operative field image of a surgical subject and a first visual annotation superimposed on a predetermined region of the first operative field image that corresponds to a physical region of the surgical subject; and generating a second image to be displayed in a second display region and including a second operative field image and a second visual annotation image superimposed on an estimated region of the second operative field image that corresponds to the physical region of the surgical subject.

(22)

A surgical assistance system including:

an endoscope including an imager that captures a second operative field image of a surgical subject;

circuitry configured to generate a first image to be displayed in a first display region and including a first operative field image of the surgical subject and a first visual annotation image superimposed on a predetermined region of the first operative field image that corresponds to a physical region of the surgical subject, and generate a second image to be displayed in a second display region and including the second operative field image and a second visual annotation image superimposed on an estimated region of the second operative field image that corresponds to the physical region of the surgical subject; and a surgical tool that is moved inside the surgical subject to perform a surgical procedure on the surgical subject under the control of a healthcare worker based on the second visual annotation image in the second image.

(31)

A surgery assistance system including:

a display controller that performs control to display an operative field image in two or more display regions;

a first superimposing unit that superimposes visual information onto a specified position specified by a user on the operative field image that is displayed in a first display region of the two or more display regions; and a second superimposing unit that superimposes the visual information while tracking the specified position on the operative field image that is displayed in real time in a second display region that is different from the first display region.

(32)

The surgery assistance system according to (31), in which the display controller displays a still image instead of the operative field image that is displayed in real time in the first display region on the basis of an instruction of the user, the still image being a single prescribed frame of the operative field image, and the first superimposing unit superimposes the visual information onto the specified position specified by the user on the still image that is displayed in the first display region.

(33)

The surgery assistance system according to (31), in which the first superimposing unit superimposes the visual information onto the specified position specified by the user on the operative field image that is displayed in real time in the first display region.

(34)

The surgery assistance system according to (31), in which the display controller displays the operative field image in a past for a prescribed time period in the first display region, and the first superimposing unit superimposes the visual information onto the specified position specified by the user on the operative field image in the past that is displayed in the first display region.

(35)

The surgery assistance system according to any of (31) to (34), in which the display controller displays the first display region and the second display region side by side on a single display device.

(36)

The surgery assistance system according to any of (31) to (34), in which the display controller displays the first display region and the second display region in a picture-in-picture form on a single display device.

(37)

The surgery assistance system according to any of (31) to (34), in which the display controller switches and displays the first display region and the second display region on a single display device.

(38)

The surgery assistance system according to any of (31) to (34), in which the display controller displays the first display region and the second display region on separate display devices.

(39)

The surgery assistance system according to any of (31) to (38), in which the display controller switches a display and a non-display of the visual information that has been superimposed onto the operative field image that is displayed at least in the second display region on the basis of an instruction of the user.

(40)

The surgery assistance system according to any of (31) to (39), in which the first superimposing unit and the second superimposing unit superimpose the visual information in display forms that are different according to the user who has specified the specified position on the operative field image.

(41)

The surgery assistance system according to any of (31) to (40), in which the first superimposing unit and the second superimposing unit superimpose, as the visual information, at least one of a point image, a line image, or a plane image according to an operation of the user.

(42)

The surgery assistance system according to (41), in which the first superimposing unit and the second superimposing unit superimpose the visual information indicating a position in a depth direction of the operative field image on the basis of three-dimensional information that has been constructed for the operative field image.

(43)

The surgery assistance system according to any of (31) to (42), in which the display controller conducts a masking display on a region in which three-dimensional information has not been sufficiently constructed in the operative field image that is displayed in the first display region.

(44)

The surgery assistance system according to any of (31) to (42), in which in a case where the user specifies the specified position on the operative field image that is displayed in the first display region, the display controller displays a preview of a three-dimensional image in which the visual information has been superimposed onto a position that corresponds to the specified position on the operative field image.

(45)

The surgery assistance system according to any of (31) to (42), in which in a case where the specified position is specified on a region in which three-dimensional information has not been sufficiently constructed in the operative field image that is displayed in the first display region, the second superimposing unit does not superimpose the visual information onto the still image that is displayed in the second display region.

(46)

The surgery assistance system according to (45), in which in a case where the specified position is specified on the region in which the three-dimensional information has not been sufficiently constructed in the operative field image that is displayed in the first display region, the display controller displays a still image serving as a single prescribed frame of the operative field image instead of the operative field image that is displayed in real time in the first display region, and the first superimposing unit superimposes the visual information onto the specified position specified by the user on the still image that is displayed in the first display region.

(47)

The surgery assistance system according to any of (31) to (46), in which the operative field image is an image that is captured by medical equipment for observation that observes an inside of a patient's body.

(48)

The surgery assistance system according to (47), in which the medical equipment for observation is an endoscope that captures an image by using the inside of the patient's body as a subject.

(49)

The surgery assistance system according to (47), in which the medical equipment for observation is a microscope that includes an optical system that captures an optical image of a subject.

28

(50)

A display method performed by a surgery assistance system, the display method including:

performing control to display an operative field image in two or more display regions; superimposing visual information onto a specified position specified by a user on the operative field image that is displayed in a first display region of the two or more display regions; and superimposing the visual information while tracking the specified position on the operative field image that is displayed in real time in a second display region that is different from the first display region.

REFERENCE SIGNS LIST

1 Surgery assistance system
11 Endoscope
13 CCU
15 Display device
100 Surgery assistance system
110 Sensing unit
130 Information processing device
131 Image data generator
132 Display controller
133 Specified position calculator
134 Three-dimensional surface map data storage
141 First superimposing unit
142 Second superimposing unit
150 Display device
151 First display region
152 Second display region

The invention claimed is:

1. A biological image processing apparatus comprising:
circuitry configured to
generate three-dimensional information indicating a three-dimensional structure of a biological subject;
receive, during a procedure, a first visual annotation image on a specified position in an operative field of a first operative field image that corresponds to a physical region of the biological subject;
according to a freeze mode input from a user interface device, generate a first image as a still image obtained from a moving image of an inside of the biological subject, wherein the first image includes the first operative field image of the biological subject and the first visual annotation image superimposed on the specified position;
according to a writing mode input from the user interface device, receive information associating the first visual annotation image with the physical region of the biological subject;
estimate a position of an imager that captures the second operative field image of the biological subject, wherein the imager is included in an endoscope that captures the second operative field image as a moving image of an inside of the biological subject; and
generate a second image by superimposing a second visual annotation image on a portion of the three-dimensional structure of the biological subject that corresponds to an estimated region of the second operative field image that is estimated to correspond to the physical region of the biological subject based on the estimated movement of the imager and the generated three-dimensional information, wherein the second operative field image is an image subsequent to the first operative field image.

2. The biological image processing apparatus according to claim 1, wherein:

the generated three-dimensional information of the biological subject includes time information indicating a generation/update time of the corresponding three-dimensional information.

3. The biological image processing apparatus according to claim 1, wherein:

the first visual annotation image is input by an input device configured to be used by a first user to input the first visual annotation image on a first display region that displays the first image without obscuring a view of a second display region that displays the second image by a second user.

4. The biological image processing apparatus according to claim 3, wherein:

the input device to input the first visual annotation image is configured to be used by the first user to identify the physical region of the biological subject as a target for an action to be performed on the biological subject; and the second visual annotation image in the second display region is configured to be used by the second user to control execution of the action on the physical region of the biological subject.

5. The biological image processing apparatus according to claim 3, wherein:

the first display region is displayed on a first display device; and the second display region is displayed on a second display device.

6. The biological image processing apparatus according to claim 3, wherein:

the first display region is displayed in a first window area of a display; and the second display region is displayed in a second window area of the display.

7. The biological image processing apparatus according to claim 1, wherein the circuitry is further configured to update the second image to maintain the correspondence between the second visual annotation superimposed on the estimated region of the second operative field image and the physical region of the subject during a movement of the imager or a movement of the physical region of the biological subject.

8. The biological image processing apparatus according to claim 1, wherein the circuitry includes a programmable processor.

9. The biological image processing apparatus according to claim 1, wherein the second operative field image includes a moving image of the biological subject that indicates a movement of the biological subject in real-time.

10. The biological image processing apparatus according to claim 9, wherein the circuitry is further configured to obtain the first operative field image from the moving image of the biological subject.

11. The biological image processing apparatus according to claim 1, wherein the circuitry is further configured to receive information regarding the first visual annotation image from an input device operated using a first display region that display the first image.

12. The biological image processing apparatus according to claim 1, wherein the second operative field image is a moving image that indicates a movement of at least the biological subject and the second visual annotation image moves with the movement of at least the biological subject to maintain the correspondence between the estimated region of the second operative field image and the physical region of the biological subject.

13. The biological image processing apparatus according to claim 1, wherein the circuitry is further configured to:

generate the second visual annotation image including an indication of a position in a depth direction of the second operative field image on the basis of the generated three-dimensional information.

14. The biological image processing apparatus according to claim 1, wherein the circuitry is further configured to:

conduct a masking display on a region of the first image in which the generated three-dimensional information has not been sufficiently constructed.

15. The biological image processing apparatus according to claim 14, wherein the circuitry is further configured to:

in a case where the estimated region of the second operation field image that corresponds to the physical region of the biological subject includes the region of the first image in which the generated three-dimensional information has not been sufficiently constructed, the second image is generated without superimposing at least a portion of the second visual annotation image.

16. The biological image processing apparatus according to claim 1, wherein the biological subject is a surgical subject.

17. The biological image processing apparatus according to claim 1, wherein the first image is a still image and the second image is a live image.

18. A biological image processing apparatus comprising:

circuitry configured to receive, during a procedure, a first visual annotation image on a specified position in an operative field of a first operative field image that corresponds to a physical region of a biological subject;

generate a first image and including the first operative field image of the biological subject and the first visual annotation image superimposed on the specified position, track the specified position over time;

generate a second image and including a second operative field image and a second visual annotation image superimposed on estimated region of the second operative field image that corresponds the physical region of the biological subject to the physical region of the biological subject based on a track of the specified position such that the second visual annotation image is superimposed in a same position on the physical region of the biological subject as the first visual annotation image, wherein the second operative field image is an image subsequent to the first operative field image;

conduct a masking display on a region of the first image in which the generated three-dimensional information has not been sufficiently constructed;

in a case where the estimated region of the second operation field image that corresponds to the physical region of the biological subject includes the region of the first image in which the generated three-dimensional information has not been sufficiently constructed, the second image is generated without superimposing at least a portion of the second visual annotation image; and in a case where the estimated region of the second operation field image that corresponds to the physical region of the biological subject includes the region of the first image in which the generated three-dimensional information has not been sufficiently constructed, the first image is displayed as a still image instead of a moving image.

19. A endoscopic image processing system comprising:

an endoscope including an imager that captures a second operative field image of a biological subject;

circuitry configured to generate three-dimensional information indicating a three-dimensional structure of the biological subject:

receive, during a procedure, a first visual annotation image on a specified position in an operative field of a first operative field image that corresponds to a physical region of the biological subject;

according to a freeze mode input from a user interface device, generate a first image as a still image obtained from a moving image of an inside of the biological subject, wherein the first image includes the first operative field image of the biological subject and the first visual annotation image superimposed on the specified position;

according to a writing mode input from the user interface device, receive information associating the first visual annotation image with the physical region of the biological subject;

generate a second image by superimposing a second visual annotation image on a portion of the three-dimensional structure of the biological subject that corresponds to an estimated region of the second operative field image that is estimated to correspond to the physical region of the biological subject based on the estimated movement of the imager and the generated three-dimensional information; and a surgical tool that is moved inside the biological subject to perform a surgical procedure on the biological subject under the control of a healthcare worker based on the second visual annotation image in the second image based on a track of the specified position, wherein the second operative field image is an image subsequent to the first operative field image.

* * * * *